United States Patent [19]

Flynn et al.

[11] Patent Number: 5,238,932

[45] Date of Patent: Aug. 24, 1993

[54] MERCAPTOACETYLAMIDE TRICYCLIC DERIVATIVES USEFUL AS INHIBITORS OF ENKEPHALINASE

[75] Inventors: Gary A. Flynn; Alan M. Warshawsky, both of Cincinnati, Ohio

[73] Assignee: Merrell Dow Pharmaceuticals Inc., Cincinnati, Ohio

[21] Appl. No.: 886,029

[22] Filed: May 20, 1992

[51] Int. Cl.⁵ .................... A61K 31/55; C07D 495/06
[52] U.S. Cl. .................................. 514/214; 540/521
[58] Field of Search ................. 540/522, 521; 514/214

[56] References Cited

U.S. PATENT DOCUMENTS

| | | | |
|---|---|---|---|
| 4,415,496 | 11/1983 | Harris et al. | 540/523 |
| 4,512,924 | 4/1985 | Attwood et al. | 544/232 |
| 4,584,294 | 4/1986 | Ruyle | 514/214 |
| 4,658,024 | 4/1987 | Attwood et al. | 544/232 |
| 4,772,701 | 9/1988 | Attwood et al. | 544/235 |
| 4,808,713 | 2/1989 | Attwood et al. | 544/235 |
| 4,824,832 | 4/1989 | Flynn et al. | 514/214 |
| 4,973,585 | 11/1990 | Flynn et al. | 514/214 |

FOREIGN PATENT DOCUMENTS

| | | | |
|---|---|---|---|
| 0249223 | 12/1987 | European Pat. Off. | 514/214 |
| 0249224 | 12/1987 | European Pat. Off. | 514/214 |
| 9108195 | 6/1991 | World Int. Prop. O. | 514/214 |
| 9109840 | 7/1991 | World Int. Prop. O. | 514/214 |

OTHER PUBLICATIONS

Attwood, et al., J. Chem. Soc., Perkin Trans 1, 1011–1019 (1986).
Natoff, et al., Drugs of the Future 12(5):475–483 (1987).
Flynn, et al., J. Am. Chem. Soc. 109:7914–15 (1987).
Flynn, et al., Peptide Chemistry 1987: T. Shiba & S. Sakakibara (ed.), Protein Research Foundation, Osaka (1988), pp. 631–636.
Flynn, et al., Tetrahedron Letters, 31(6): 815–818 (1990).

Primary Examiner—Robert T. Bond
Attorney, Agent, or Firm—Charlotte L. Barney

[57] ABSTRACT

The present invention relates to novel mercaptoacetylamide tricyclic derivatives useful as inhibitors of enkephalinase.

21 Claims, No Drawings

MERCAPTOACETYLAMIDE TRICYCLIC DERIVATIVES USEFUL AS INHIBITORS OF ENKEPHALINASE

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as $\beta$-endorphin and the enkephalins, atrial natriuretic peptide (ANP), bradykinin and other circulating regulatory peptides.

Endorphins are naturally-occurring polypeptides which bind to opiate receptors in various areas of the brain and thereby provide an analgesic effect by raising the pain threshold. Endorphins occur in various forms including $\alpha$-endorphin, $\beta$-endorphin, $\gamma$-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins is inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration.

ANP refers to a family of naturally-occurring peptides which are involved in the homeostatic regulation of blood pressure, as well as sodium and water levels. ANPs have been found to vary in length from about 21 to about 126 amino acids with a common structural feature being one or more disulfide-looped sequences of 17 amino acids with various amino- and carboxy-terminal sequences attached to the cystine moiety. ANPs have been found to bind to specific binding sites in various tissues including kidney, adrenal, aorta, and vascular smooth muscle with affinities ranging from about 50 pico-molar (pM) to about 500 nano-molar (nM) [Needleman, *Hypertension* 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurring ANP is inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

SUMMARY OF THE INVENTION

The present invention provides novel compounds of the Formula (I)

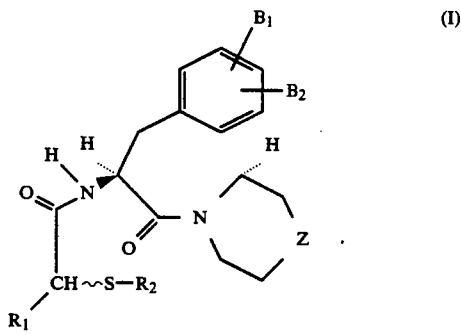

wherein
$B_1$ and $B_2$ are each independently hydrogen; hydroxy; —$OR_3$ wherein $R_3$ is a $C_1$-$C_4$ alkyl or an Ar-Y- group wherein Ar is aryl and Y is a $C_0$-$C_4$ alkyl; or, where $B_1$ and $B_2$ are attached to adjacent carbon atoms, $B_1$ and $B_2$ can be taken together with said adjacent carbons to form a benzene ring or methylenedioxy;

$R_1$ is hydrogen, $C_1$-$C_8$ alkyl, —$CH_2OCH_2CH_2OCH_3$ or an Ar-Y- group;

$R_2$ is hydrogen, acetyl, —$CH_2O$—$C(O)C(CH_3)_3$ or benzoyl; and

Z is —O—, —S—,

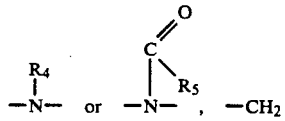

or a bond wherein $R_4$ is hydrogen, a $C_1$-$C_4$ alkyl or an Ar-Y- group and $R_5$ is —$CF_3$, $C_1$-$C_{10}$ alkyl or an Ar-Y- group; and the pharmaceutically acceptable salts and individual optical isomers thereof thereof.

The present invention further provides a method of inhibiting enkephalinase in a patient in need thereof comprising administering to said patient an effective enkephalinase inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1$-$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "$C_1$-$C_8$ alkyl" refer to saturated straight or branched chain hydrocarbyl radicals of one to eight carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl. The term "$C_1$–$C_{10}$ alkyl" refer to saturated straight or branched chain hydrocarbyl radicals of one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl, nonyl, or decyl and the like. The term "Boc" refers to t-butyloxycarbonyl.

As used herein, the term "Ar—Y—" refers to a radical wherein Ar is an aryl group and Y is a $C_0$–$C_4$ alkyl. The term "Ar" refers to a phenyl or naphthyl group unsubstituted or substituted with from one to three substituents selected from the group consisting of methylenedioxy, hydroxy, $C_1$–$C_4$ alkoxy, amino, nitro, fluoro and chloro. The term "$C_1$–$C_4$ alkoxy" refers to a saturated straight or branched chain hydrocarboxy radical of one to four carbon atoms and includes methoxy, ethoxy, propoxy, isopropoxy, n-butoxy, isobutoxy, tertiary butoxy and the like. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar-Y-" are phenyl, naphthyl, phenylmethyl or benzyl, phenylethyl, 3,4-methylenedioxyphenyl, m-aminophenyl, m-nitrophenyl, p-aminophenyl, p-nitrophenyl, p-methoxybenzyl, p-fluorobenzyl and p-chlorobenzyl.

As used herein, the designation "ss" refers to a bond to a chiral atom for which the stereochemistry is not designated.

Compounds of Formula (I) wherein Z is $NR_4$ and $R_4$ is hydrogen can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salacylic, 2-phenoxybenzoic and sulfonic acids such as methane sulfonic, trifluoromethane sulfonic, 2-hydroxyethane sulfonic acid and p-toluenesulfonic acid.

The compounds of Formula (I) wherein Z is —$CH_2$—, —O—, —S—, a bond or —$NR_4$— wherein $R_4$ is hydrogen can be prepared by utilizing procedures and techniques well known and appreciated by one of ordinary skill in the art. A general synthetic scheme for preparing these compounds is set for in Scheme A wherein all substituents are as previously defined unless otherwise defined.

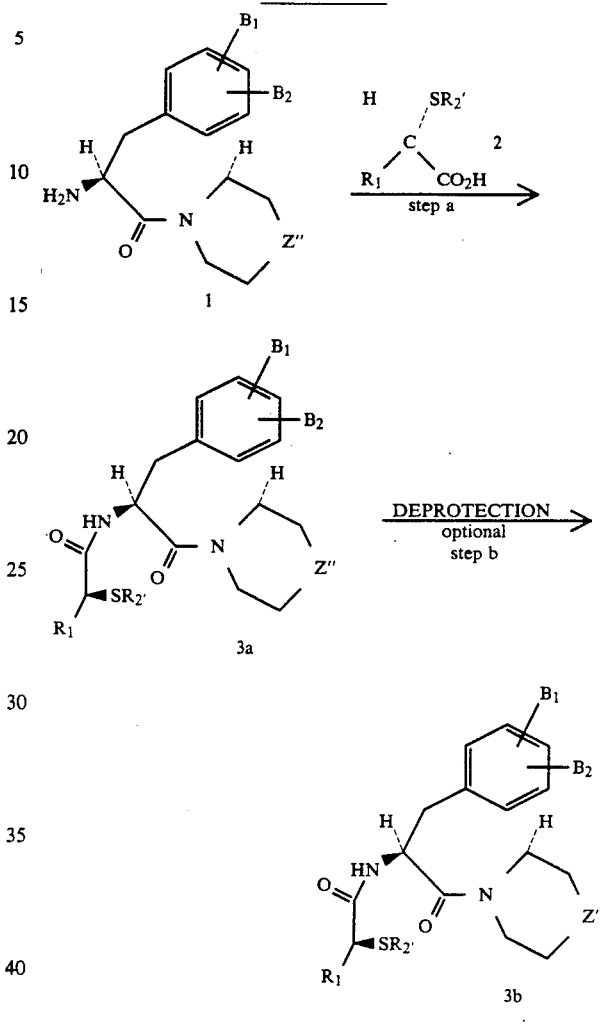

$R_2' = COCH_3$, COPh
$Z'' =$ —$CH_2$—, —O—, —S—, a bond or -N-Boc-
$Z' =$ —NH—

Scheme A provides a general synthetic procedure for preparing compounds of Formula (I) wherein Z is —$CH_2$—, —O—, —S—, a bond or —$NR_4$— wherein $R_4$ is hydrogen.

In step a, the appropriate amino tricyclic compound of structure (1) wherein Z is —$CH_2$—, —O—, —S—, a bond or -N-Boc is reacted with the appropriate (S)-thioacetate or (S)-thiobenzoate of structure (2) to give the corresponding (S)-thioacetate or (S)-thiobenzoate tricyclic compound of structure (3a) wherein Z is —$CH_2$—, —O—, —S—, a bond or -N-Boc. For example, the appropriate amino tricyclic compound of structure (1) wherein Z is —$CH_2$—, —O—, —S—, a bond or -N-Boc can be reacted with the appropriate (S)-thioacetate or (S)-thiobenzoate compound of structure (2) in the presence of a coupling reagent such as EEDQ (2-ethoxy-2-ethoxycarbonyl-1,2-dihydro-quinoline), DCC (1,3-dicyclohexylcarodiimide), or diethylcyanophosponate in a suitable aprotic solvent, such as methylene chloride to give the appropriate (S)-thioacetate or (S)-thiobenzoate tricyclic compound of structure (3a) wherein Z is —$CH_2$—, —O—, —S—, a bond or -N-Boc.

Alternatively, the appropriate amino tricyclic compound of structure (1) wherein Z is —CH₂—, —O—, —S—, a bond or -N-Boc is reacted with the appropriate (R)-thioacetate or (R)-thiobenzoate to give the corresponding (R)-thioacetate or (R)-thiobenzoate tricyclic compound wherein Z is —CH₂—, —O—, —S—, a bond or -N-Boc as described previously in step a.

In addition, the appropriate amino tricyclic compound of structure (1) wherein Z is —CH₂—, —O—, —S—, a bond or -N-Boc is reacted with the appropriate racemic mixture of thioacetate or thiobenzoate compounds wherein Z is —CH₂—, —O—, —S—, a bond or -N-Boc to give the corresponding diastereomeric mixture of thioacetate or thiobenzoate tricyclic compound wherein Z is —CH₂—, —O—, —S—, a bond or -N-Boc as described previously in step a.

In optional step b, the Boc protecting group on those (S)-thioacetate or (S)-thiobenzoate tricyclic compounds of structure (3a) wherein Z is -N-Boc, is removed by techniques and procedures well known and appreciated by one of ordinary skill in the art, such as dilute hydrochloric acid to give the corresponding (S)-thioacetate or (S)-thiobenzoate tricyclic compound of structure (3b) wherein Z is —NR₄— wherein R₄ is hydrogen. Alternatively, for those (R)-thioacetate or (R)-thiobenzoate tricyclic compounds wherein Z is -N-Boc, the Boc protecting group is removed as described above for the (S)-thioacetate or (S)-thiobenzoate tricyclic compounds of structure (3a) wherein Z is -N-Boc to give the corresponding (R)-thioacetate or (R)-thiobenzoate tricyclic compound wherein Z is —NR₄— wherein R₄ is hydrogen. In addition, for the corresponding diastereomeric mixture of thioacetate or thiobenzoate tricyclic compounds wherein Z is -N-Boc, the Boc protecting groups are removed as described above for the (S)-thioacetate or (S)-thiobenzoate tricyclic compounds of structure (3a) wherein Z is -N-Boc to give the corresponding diastereomeric mixture of thioacetate or thiobenzoate tricyclic compound wherein Z is —NR₄— wherein R₄ is hydrogen.

As summarized in Table 1, the R₂ group on the thioacetate or thiobenzoate tricyclic compounds described above in Scheme A can be manipulated using techniques and procedures well known and appreciated by one of ordinary skill in the art.

The thioacetate or thiobenzoate functionality of the appropriate (S)-thioacetate or (S)-thiobenzoate tricyclic compounds of structure (3a) wherein Z is —CH₂—, —O—, —S—, a bond or -N-Boc can be removed with lithium hydroxide in a suitable solvent mixture such as tetrahydrofuran and methanol or with ammonia in a suitable protic solvent such as methanol, to give the appropriate (S)-thiol tricyclic compound of structures (4a) wherein Z is —CH₂—, —O—, —S—, a bond or -N-Boc. Alternatively, the thioacetate or thiobenzoate functionality of the appropriate corresponding (R)-thioacetate or (R)-thiobenzoate tricyclic compounds wherein Z is —CH₂—, —O—, —S—, a bond or -N-Boc can be removed as described above for the (S)-thioacetate or (S)-thiobenzoate tricyclic compounds of structures (3a) wherein Z is —CH₂—, —O—, —S—, a bond or -N-Boc to give the corresponding (R)-thiol tricyclic compounds wherein Z is —CH₂—, —O—, —S—, a bond or -N-Boc. In addition, the thioacetate or thiobenzoate functionalities of the appropriate corresponding diastereomeric mixture of thioacetate or thiobenzoate tricyclic compounds wherein Z is —CH₂—, —O——S—, a bond or -N-Boc can be removed as described above for the (S)-thioacetate or (S)-thiobenzoate tricyclic compounds of structures (3a) wherein Z is —CH₂—, —O—, —S—, a bond or -N-Boc to give the corresponding diastereomeric mixture of thiol tricyclic compounds wherein Z is —CH₂—, —O—, —S—, a bond or -N-Boc.

The Boc protecting group on the appropriate (S)-, (R)-, or diastereomeric mixture of thiol tricyclic compounds of structures (4) wherein Z is -N-Boc can be removed as described previously in optional step b to give the corresponding (S)-, (R)- or diastereomeric thiol tricyclic compounds of structure (4) wherein Z is NR₄ and R₄ is hydrogen.

The thiol functionality of the appropriate (S)-thiol tricyclic compounds of structures (4a) wherein Z is —CH₂—, —O—, —S— or a bond can then be converted to the corresponding (S)-pivaloyloxymethyl thioether tricyclic compound of structure (5a) wherein Z is —CH₂—, —O—, —S— or a bond using techniques and procedures well known and appreciated in the art. For example, a (S)-pivaloyloxymethyl thioether tricyclic compound of structure (5a) wherein Z is —CH₂—, —O—, —S— or a bond can be prepared by treating the (S)-thiol tricyclic compound of structure (4a) wherein Z is —CH₂—, —O—, —S— or a bond with chloromethyl pivalate in a suitable aprotic solvent, such as dimethylformamide along with a non-nucleophilic base, such as cesium carbonate. Alternatively, the thiol functionality of the appropriate corresponding (R)-thiol tricyclic compounds wherein Z is —CH₂—, —O—, —S— or a bond can be converted to the corresponding pivaloyloxymethyl thioether as described above for the (S)-thiol tricyclic compounds of structure (4a) wherein Z is —CH₂—, —O—, —S— or a bond to give the corresponding (R)-pivaloyloxymethyl thioether tricyclic compound wherein Z is —CH₂—, —O—, —S— or a bond. In addition, the thiol functionalities of the appropriate corresponding diastereomeric mixture of thiol tricyclic compounds can be converted to the corresponding pivaloyloxymethyl thioethers to give the corresponding diastereomeric mixture of pivaloyloxymethyl thioether tricyclic compounds wherein Z is —CH₂—, —O—, —S— or a bond.

The thiol functionality of the appropriate (S)-thiol tricyclic compounds of structures (4a) wherein Z is -N-Boc can be converted to the corresponding (S)-pivaloyloxymethyl thioether tricyclic compound of structure (5a) wherein Z is —NR₄— and R₄ is hydrogen using techniques and procedures well known and appreciated in the art. For example, a (S)-pivaloyloxymethyl thioether tricyclic compound of structure (5a) wherein Z is —NR₄— and R₄ is hydrogen can be prepared by treating the (S)-thiol tricyclic compound of structure (4a) wherein Z is -N-Boc, the Boc protecting group is first removed as described previously in optional step b to give the corresponding (S)-thiol tricyclic compound of structure (4a) wherein Z is —NR₄— and R₄ is hydrogen. The thiol functionality of the appropriate (S)-thiol tricyclic compound of structure (4a) wherein Z is —NR₄— and R₄ is hydrogen is then converted to the corresponding (S)-pivaloyloxymethyl thioether tricyclic compound of structure (5a) wherein Z is —NR₄— and R₄ is hydrogen with one equivalent of chloromethyl pivalate and one equivalent of a suitable non-nucleophilic base. Alternatively, the thiol functionality of the appropriate corresponding (R)-thiol tricyclic compounds wherein Z is -N-Boc can be converted to the corresponding pivaloyloxymethyl thioether as described above for the (S)-thiol tricyclic compounds of structure (4a) wherein Z is -N-Boc to give the corresponding (R)-pivaloyloxymethyl thioether tricyclic compound wherein Z is —NR4— and R4 is hydrogen. In addition, the thiol functionalities of the appropriate corresponding diastereomeric mixture of thiol tricyclic compounds can be converted to the corresponding pivaloyloxymethyl thioethers to give the corresponding diastereomeric mixture of pivaloyloxymethyl thioether tricyclic compounds wherein Z is —NR4— and R4 is hydrogen.

TABLE 1
MANIPULATION OF R2

| Compound | R2 |
|---|---|
| 3a | —COCH3 or —COPh |
| 4a | —H |
| 5a | —CH2OCOC(CH3)3 |

Scheme B provides another general synthetic procedure for preparing compounds of Formula (I) wherein Z is —CH2—, —O—, —S—, a bond or —NR4— wherein R4 is hydrogen.

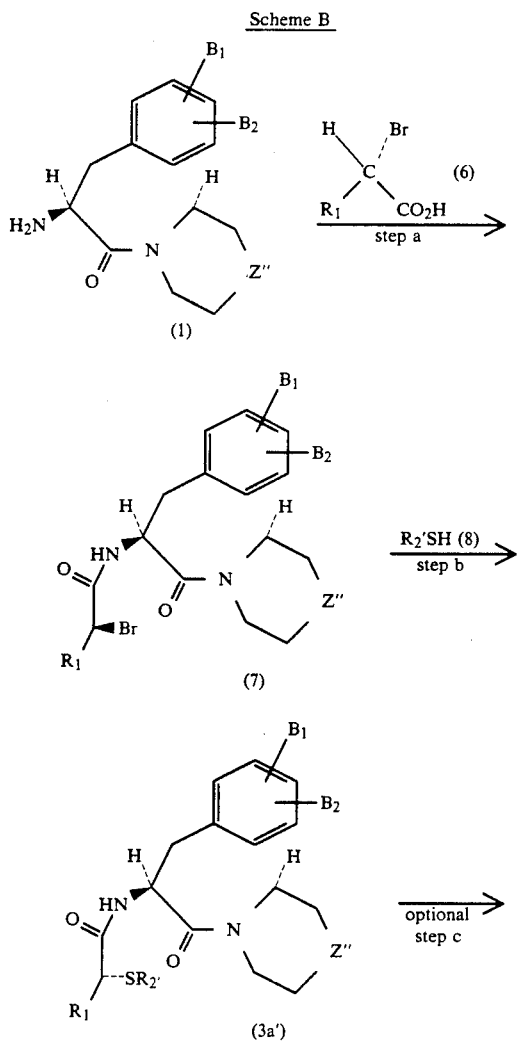

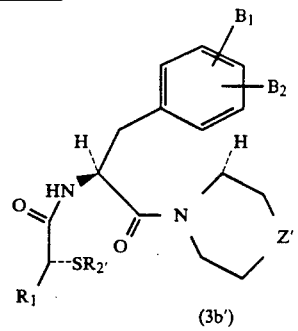

$R_2' = COCH_3$, COPh
$Z'' = $ —CH2—, —O—, —S—, a bond or -N-Boc-
$Z' = $ —CH2—, —O—, —S—, a bond or -NH- In step a, the appropriate amino tricyclic compound of structure (1) wherein Z is —CH2—, —O—, —S—, a bond or -N-Boc is reacted with the appropriate (S)-bromoacid of structure (6) to give the corresponding (S)-bromoamide tricyclic compound of structure (7) wherein Z is —CH2—, —O—, —S—, a bond or -N-Boc as described previously in Scheme A, step a.

Alternatively the appropriate amino tricyclic compound of structure (1) wherein Z is —CH2—, —O—, —S—, a bond or -N-Boc is reacted with the appropriate (R)-bromoacid to give the corresponding (R)-bromoamide tricyclic compound wherein Z is —CH2—, —O—, —S—, a bond or -N-Boc as described previously in Scheme A, step a.

In addition, the appropriate amino tricyclic compound of structure (1) wherein Z is —CH2—, —O—, —S—, a bond or -N-Boc is reacted with the appropriate racemic mixture of the bromoacid to give the corresponding diastereomeric mixture of bromoamide tricyclic compound wherein Z is —CH2—, —O—, —S—, a bond or -N-Boc as described previously in Scheme A, step a.

In step b, the (S)-bromo functionality of the appropriate (S)-bromoamide tricyclic compound of structure (7) wherein Z is —CH2—, —O—, —S—, a bond or -N-Boc is converted to the corresponding (R)-thioacetate or (R)-thiobenzoate tricyclic of structure (3b) wherein Z is —CH2—, —O—, —S—, a bond or -N-Boc.

For example, the appropriate (S)-bromoamide tricyclic compound of structure (7) wherein Z is —CH2—, —O—, —S—, a bond or -N-Boc is reacted with thiolacetic acid or thiolbenzoic acid of structure (8) in the presence of a base, such as cesium carbonate. The reactants are typically contacted in a suitable organic solvent such as a mixture of dimethylformamide and tetrahydrofuran. The reactants are typically stirred together at room temperature for a period of time ranging from 1 to 8 hours. The resulting (R)-thioacetate or (R)-thiobenzoate tricyclic compounds of structure (3a') wherein Z is —CH2—, —O—, —S—, a bond or -N-Boc is recovered from the reaction zone by extractive methods as is known in the art. It may be purified by chromatography.

Alternatively, the (R)-bromo functionality of the appropriate (R)-bromoamide tricyclic compound wherein Z is —CH2—, —O—, —S—, a bond or -N-Boc is converted to the corresponding (S)-thioacetate or (S)-thiobenzoate tricyclic compound wherein Z is —CH2—, —O—, —S—, a bond or -N-Boc as described above for the (S)-bromoamide tricyclic compound of structure (7) wherein Z is —CH$_2$—, —O—, —S—, a bond or -N-Boc.

In addition, the bromo functionality of the appropriate diastereomeric mixture of the bromoamide tricyclic compounds wherein Z is —CH$_2$—, —O—, —S—, a bond or -N-Boc is converted to the corresponding diastereomeric mixture of thioacetate or thiobenzoate tricyclic compounds wherein Z is —CH$_2$—, —O—, —S—, a bond or -N-Boc as described above for the (S)-bromoamide tricyclic compound of structure (7) wherein Z is —CH$_2$—, —O—, —S—, a bond or -N-Boc.

In optional step c, the Boc protecting group on those (R)-thioacetate or (R)-thiobenzoate tricyclic compounds of structure (3a') wherein Z is -N-Boc, is removed as described previously in Scheme A, optional step b to give the corresponding (R)-thioacetate or (R)-thiobenzoate tricyclic compounds of structure (3b') wherein Z is —NR$_4$— wherein R$_4$ is hydrogen. Alternatively, for those (S)-thioacetate or (S)-thiobenzoate tricyclic compounds of structure (3a) wherein Z is -N-Boc, the Boc protecting group is removed as described above for the (R)-thioacetate or (R)-thiobenzoate tricyclic compounds of structure (3a') wherein Z is -N-Boc to give the corresponding (S)-thioacetate or (S)-thiobenzoate tricyclic compounds of structure (3b) wherein Z is —NR$_4$— wherein R$_4$ is hydrogen. In addition, for the corresponding diastereomeric mixture of thioacetate or thiobenzoate tricyclic compounds wherein Z is -N-Boc, the Boc protecting groups are removed as described above for the (R)-thioacetate or (R)-thiobenzoate tricyclic compounds of structure (3a') wherein Z is -N-Boc to give the corresponding diastereomeric mixture of thioacetate or thiobenzoate tricyclic compound wherein Z is —NR$_4$— wherein R$_4$ is hydrogen.

The group R$_2$ may be manipulated by techniques and procedures well known and appreciated in the art and described previously in Scheme A and Table 1.

The compounds of Formula (I) wherein Z is —NR$_4$— wherein R$_4$ is other than hydrogen or wherein Z is —NCOR$_5$— can be prepared by techniques and procedures well known and appreciated by one of ordinary skill in the art. A general synthetic procedure for preparing these compounds is set forth in Scheme C. In Scheme C, all substituents unless otherwise indicated are as previously defined.

Scheme C

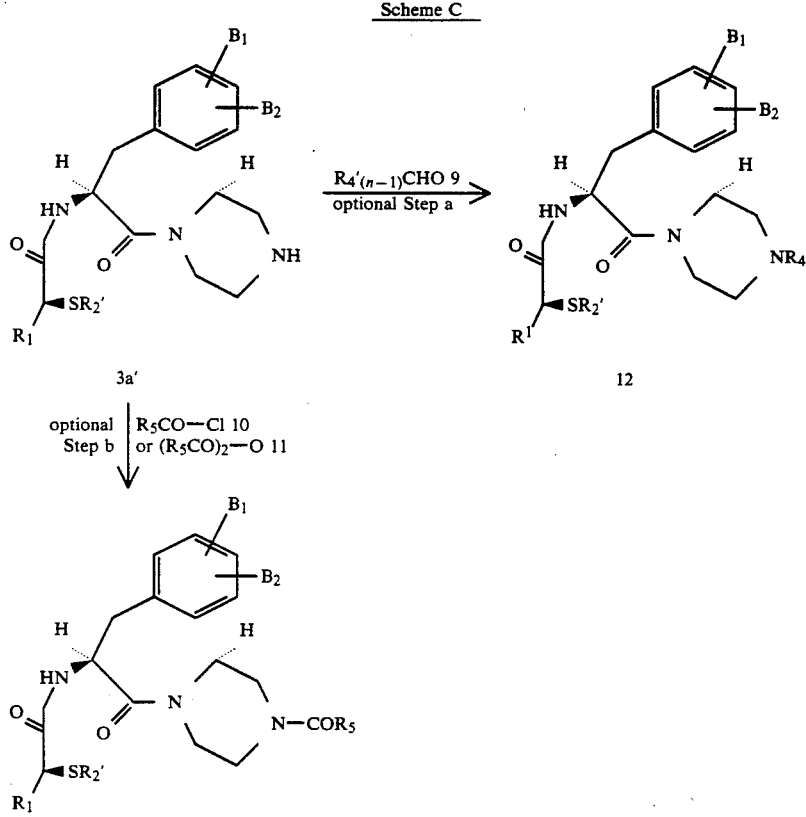

R$_4'$ = C$_1$-C$_4$ alkyl or an Ar-Y group
R$_2'$ = COCH$_3$, COPh

In optional step a, the amino functionality of the appropriate (S)-thioacetate or (S)-thiobenzoate tricyclic compound of structure (3a') wherein Z is —NR$_4$— wherein R$_4$ is hydrogen is subjected to reductive alkylation with the appropriate aldehyde of structure (9) using sodium cyanoborohydride, as is well known in the art, to give the corresponding N-alkyl-(S)-thioacetate or N-alkyl-(S)-thiobenzoate tricyclic compound of structure (12).

Alternatively, the amino functionality of the appropriate (R)-thioacetate or (R)-thiobenzoate tricyclic compound wherein Z is —NR$_4$- wherein R$_4$ is hydrogen is subjected to reductive alkylation as described above for the (S)-thioacetate or (S)-thiobenzoate tricyclic compound of structure (3a') wherein Z is —NR$_4$— wherein R$_4$ is hydrogen to give the corresponding N- alkyl-(R)-thioacetate or N-alkyl-(R)-thiobenzoate tricyclic compound.

In addition, the amino functionality of the appropriate diastereomeric mixture of thioacetate or thiobenzoate tricyclic compound wherein Z is —NR$_4$— wherein R$_4$ is hydrogen is subjected to reductive alkylation as described above for the (S)-thioacetate or (S)-thiobenzoate tricyclic compound of structure (3a') wherein Z is —NR$_4$— wherein R$_4$ is hydrogen to give the corresponding diastereomeric mixture of N-alkylthioacetate or N-alkyl-thiobenzoate tricyclic compound.

In optional step b, the amino functionality of the appropriate (S)-thioacetate or (S)-thiobenzoate tricyclic compound of structure (3a') wherein Z is —NR$_4$— wherein R$_4$ is hydrogen is acylated using the appropriate acyl chloride of structure (10) or the appropriate anhydride of structure (11), as is well known in the art, to give the corresponding N-acyl-(S)-thioacetate or N-acyl-(S)-thiobenzoate tricyclic compound of structure (13).

Alternatively, the amino functionality of the appropriate (R)-thioacetate or (R)-thiobenzoate tricyclic compound wherein Z is —NR$_4$— wherein R$_4$ is hydrogen is acylated as described above for the (S)-thioacetate or (S)-thiobenzoate tricyclic compound of structure (3a') wherein Z is —NR$_4$— wherein R$_4$ is hydrogen to give the corresponding N-acyl-(R)-thioacetate or N-acyl-(R)-thiobenzoate tricyclic compound.

In addition, the amino functionality of the appropriate diastereomeric mixture of thioacetate or thiobenzoate tricyclic compound wherein Z is —NR$_4$— wherein R$_4$ is hydrogen is acylated as described above for the (S)-thioacetate or (S)-thiobenzoate tricyclic compound of structure (3a') wherein Z is —NR$_4$— wherein R$_4$ is hydrogen to give the corresponding diastereomeric mixture of N-acyl-thioacetate or N-acyl-thiobenzoate tricyclic compound.

The groups R$_2$ may be manipulated by techniques and procedures well known and appreciated in the art and described previously in Scheme A and shown in Table 1.

Amino tricyclic compounds of structure (1) wherein Z is —CH$_2$—, —O—, —S—, a bond or -N-Boc may be prepared as described in Scheme D. In Scheme D, all substituents unless otherwise indicated are as previously defined.

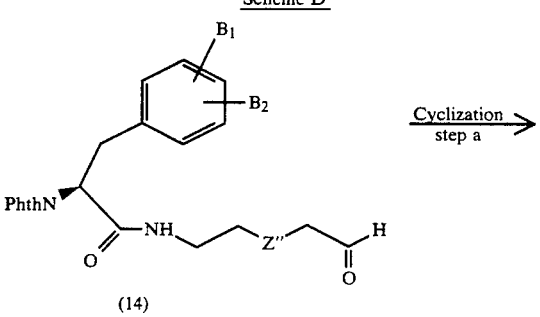

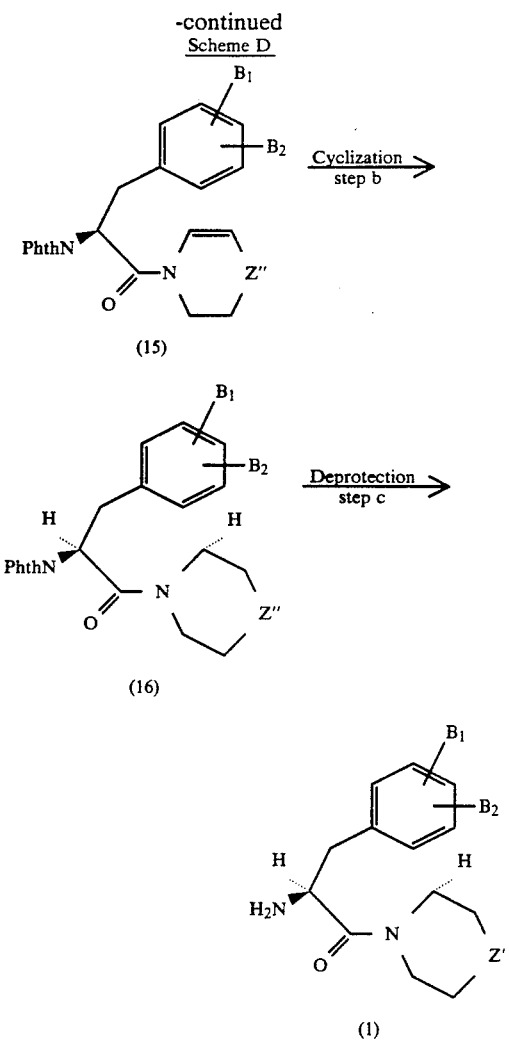

Z''=—CH$_2$—, —O—, —S—, a bond or —NCOCF$_3$—
Z'=—CH$_2$—, —O—, —S—, a bond or -N-Boc- In step a, the appropriate aldehyde of structure (14) can be cyclized to the appropriate enamine of structure (15) by acid catalysis. For example, the appropriate aldehyde of structure (14) can be cyclized to the appropriate enamine of structure (15) by treatment with trifluoroacetic acid in a suitable aprotic solvent, such as methylene chloride.

In step b, the appropriate enamine of structure (15) can be converted to the corresponding tricyclic compound of structure (16) by an acid catalyzed Friedel-Crafts reaction. For example, the appropriate enamine of structure (15) can be converted to the corresponding tricyclic compound of structure (16) by treatment with a mixture of trifluoromethane sulfonic acid and trifluoroacetic anhydride in a suitable aprotic solvent, such as methylene chloride.

In step c, for those tricyclic compounds of structure (16) wherein Z is —CH$_2$—, —O—, —S— or a bond, the phthalimide protecting group of the appropriate tricyclic compound of structure (16) wherein Z is —CH$_2$—, —O—, —S— or a bond can be removed using techniques and procedures well known in the art. For example, the phthalimide protecting group of the appropriate tricyclic compound of structure (16) wherein Z is —CH$_2$—, —O—, —S— or a bond can be removed using hydrazine monohydrate in a suitable protic solvent such as methanol, to give the corresponding amino tricyclic compound of structure (1) wherein Z is —CH$_2$—, —O—, —S— or a bond.

For those tricyclic compounds of structure (16) wherein Z —NCOCF$_3$, the trifluoroacetamide functionality is removed according to the procedure described in *Tetrahedron Letters* 32(28) 3301-3304 1991 to give the corresponding tricyclic compounds of structure (16) wherein Z -NH. The amino functionality of the appropriate tricyclic compounds of structure (16) wherein Z -NH is protected with a Boc protecting group by techniques and procedures well known and appreciated in the art to give the corresponding tricyclic compounds of structure (16) wherein Z -N-Boc. The phthalimide protecting group of the appropriate tricyclic compounds of structure (16) wherein Z -N-Boc is then removed using hydrazine as described above in step c to give the corresponding amino tricyclic compound of structure (1) wherein Z -N-Boc.

Starting materials for use in Schemes A through D are readily available to one of ordinary skill in the art.

The following examples present typical syntheses as described in Schemes A through D. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C" refers to degrees Celsius; "mm Hg" refers to millimeters of mercury; "μL" refers to microliters; "μg" refers to micrograms; and "μM" refers to micromolar.

EXAMPLE 1

[4α, 7α(R*), 12bβ]-7-[(1-Oxo-2(R)-benzoylthio-3-phenylpropyl)amino]-1,2,3,4,6,7,8,12b-octahydro-6-oxopyrido[2,1-a][2]benzazepine Scheme D, step a: (R*,R*)]-N-[2-(1,3-Dihydro-1,3-dioxo-2H-isoindol-2-yl)-1-oxo-3-phenylpropyl]-1,2,3,4-tetrahydro-2-pyridine Mix 5-bromo-1-pentene (31.2 g, 0.209 mol) and potassium cyanide (16.8 g, 0.257 mol) in ethylene glycol (85 mL) and heat at 100° C. for 2 hours. Cool, dilute with water (100 mL) and extract into ethyl ether (100 mL). Wash with saturated sodium hydrogen carbonate (35 mL), dry (Na$_2$SO$_4$) and distill to give 5-hexenylnitrile as a colorless liquid (16.3 g, 82%); bp 150°-156° C.

Suspend lithium aluminum hydride (6.5 g, 0.17 mol) in ethyl ether (350 mL) and add, by dropwise addition over 30 minutes, 5-hexenylnitrile (16.3 g, 0.171 mol). Stir at room temperature for 2 hours, cool in an ice bath and add sequentially, by very slow addition, water (6.8 mL), 20% sodium hydroxide (5.2 mL), then water (24 mL). Decant the ethereal phase and wash the white salts with ether. Combine the ethereal phases and distill at atm. pressure to give 5-hexenylamine as a colorless liquid (10.7 g, 63%); bp 125°-135° C.

Dissolve 5-hexenylamine (0.88 g, 8.9 mmol) in methylene chloride (50 mL) and treat first with N-phthaloyl-(S)-phenylalanine (2.95 g, 10.0 mmol), then with EEDQ (2.47 g, 10.0 mmol) and stir at room temperature for 6 hours. Evaporate the solvent in vacuo, dissolve the residue in ethyl acetate (75 mL) and wash with 5% sulfuric acid (25 mL), saturated sodium hydrogen carbonate (25 mL) and brine (25 mL). Dry (Na$_2$SO$_4$), evaporate the solvent in vacuo and purify by chromatography (hexane/ethyl acetate) to give 2-(1,3-dihydro-1,3-dioxo-2H-isoindol-2-yl)-1-oxo-3-phenylpropyl-5-hexenylamine as a white solid (1.8 g).

Dissolve 2-(1,3-dihydro-1,3-dioxo-2H-isoindol-2-yl)-1-oxo-3-phenylpropyl-5-hexenylamine (1.2 g, 3.19 mmol) in methylene chloride (40 mL) and methanol (4 mL) and cool to −78° C. under a nitrogen atmosphere. Treat with ozone until a blue color persists, degas with nitrogen for 20 minutes and add pyridine (0.2 mL). Quench with dimethylsulfide (4 mL) and stir overnight at room temperature. Dilute with methylene chloride (75 mL) and wash with 5% sulfuric acid (40 mL) and brine (40 mL). Dry (Na$_2$SO$_4$), evaporate the solvent in vacuo and purify by chromatography (hexane/ethyl acetate) to give 2-(1,3-dihydro-1,3-dioxo-2H-isoindol-2-yl)-1-oxo-3-phenylpropyl-5-oxo-pentylamine as a white solid (972 mg, 80%).

Dissolve 2-(1,3-dihydro-1,3-dioxo-2H-isoindol-2-yl)-1-oxo-3-phenylpropyl-5-oxo-pentylamine (153 mg, 0.404 mmol) in anhydrous methylene chloride (7 mL) and treat with trifluoroacetic acid (0.04 mL, 0.5 mmol). Stir at room temperature for 3 hours, partition between methylene chloride (25 mL) and saturated sodium hydrogen carbonate (15 mL). Dry (Na$_2$SO$_4$), evaporate the solvent in vacuo and purify by chromatography (hexane/ethyl acetate) to give the title compound as a white solid (623 mg, 83%).

Scheme D, step b: [4α, 7α(R*), 12bβ]-7-[(1,3-Dihydro-1,3-dioxo-2H-isoindol-2-yl)]-1,2,3,4,6,7,8,12b-octahydro-6-oxopyrido[2,1-a][2]benzazepine Dissolve (R*,R*)]-N-[2-(1,3-dihydro-1,3-dioxo-2H-isoindol 2-yl)-1-oxo-3-phenylpropyl]-1,2,3,4-tetrahydro-2-pyridine (623 mg, 1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL). Dry (Na$_2$SO$_4$), evaporate the solvent in vacuo and purify by chromatography (hexane/ethyl acetate) to give the title compound as a white solid (600 mg, 96%).

Scheme D, step c: [4α, 7α(R*), 12bβ]-7-(Amino)-2,3,4,6,7,8,12b-octahydro-6-oxopyrido[2,1-a][2]benzazepine Dissolve [4α, 7α(R*), 12bβ]-7-[(1,3-dihydro-1,3-dioxo-2H-isoindol-2-yl)]-1,2,3,4,6,7,8,12b-octahydro-6-oxopyrido[2,1-a][2]benzazepine (669 mg, 1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO$_4$ and evaporate the solvent in vacuo to give the title compound as a white solid (407 mg, 95%).

Scheme A, step a: [4α, 7α(R*), 12bβ]-7-[(1-Oxo-2(R)-benzoylthio-3-phenylpropyl)amino]-1,2,3,4,6,7,8,12b-octahydro-6-oxopyrido[2,1-a][2]benzazepine Dissolve [4α, 7α(R*), 12bβ]-7-(amino)-1,2,3,4,6,7,8,12b-octahydro-6-oxopyrido[2,1-a][2]benzazepine (136 mg, 0.59 mmol), (R)-3-phenyl-2-benzoylthiopropionic acid (250 mg, 0.87 mmol) and EEDQ (220 mg, 0.89 mmol) in methylene chloride (5 mL). Stir at room temperature for 18 hours, evaporate the solvent in vacuo and dilute the residue with ethyl acetate (25 mL). Wash with 5% sulfuric acid (10 mL), saturated sodium hydrogen carbonate (10 mL) and brine (10 mL). Dry (Na₂SO₄), evaporate the solvent in vacuo and purify by chromatography (hexane/ethyl acetate) to give the title compound as a white foam (274 mg, 93.2%).

EXAMPLE 2-MDL 101,705

[4α, 7α(R*), 12bβ]-7-[(1-Oxo-2(R)-thio-3-phenylpropyl)amino]-1,2,3,4,6,7,8,12b-octahydro-6-oxopyrido[2,1-a][2]benzazepine Dissolve [4α, 7α(R*), 12bβ]-7-[(1-oxo-2(R)-benzoylthio-3-phenylpropyl)amino]-1,2,3,4,6,7,8,12b-octahydro-6-oxopyrido[2,1-a][2]benzazepine (274 mg, 0.550 mmol) in a degassed mixture of tetrahydrofuran (5 mL) and methanol (5 mL). Cool in an ice bath and treat with lithium hydroxide (1 mL of a 1.0M solution). Stir under an argon atmosphere for 1 hour and add hydrochloric acid (1.5 mL of a 1M solution). Partition between methylene chloride (75 mL) and water (30 mL); separate the organic phase and dry (Na₂SO₄). Evaporate the solvent in vacuo and purify by chromatography (methylene chloride/ethyl acetate) to give the title compound as a white solid (173 mg, 79.7%).

EXAMPLE 3

[4α, 7α(R*), 12bβ]-7-[(1-Oxo-2(S)-acetylthio-3-phenylpropyl)amino]-1,2,3,4,6,7,8,12b-octahydro-6-oxopyrido[2,1-a][2]benzazepine Scheme B, step a: [4α, 7α(R*), 12bβ]-7-[(1-Oxo-2(R)-bromo-3-phenylpropyl)amino]-1,2,3,4,6,7,8,12b-octahydro-6-oxopyrido[2,1-a][2]benzazepine Mix D-phenylalanine (186.4 g, 1.128 mol) and 49% hydrobromic acid (372.8 g), cool to −5° C. and add, by dropwise addition, a solution of sodium nitrite (77.9 g) in water (565 mL) over a period of about 1 hour (vigorous gas evolution). Stir at −5° C. to 0° C. for 4 hours, extract into ethyl ether (3×1 L), dry (MgSO₄) and evaporate the solvent in vacuo. Purify by chromatography (5% acetic acid/95% methylene chloride) and distillation to give 3-phenyl-2(R)-bromopropionic acid (112 g, 43%); bp 128°-135° C.@0.25 torr.

Dissolve [4α, 7α(R*), 12bβ]-7-(amino)-1,2,3,4,6,7,8,12b-octahydro-6-oxopyrido[2,1-a][2]benzazepine (0.38 mg, 1.65 mmol), 3-phenyl-2(R)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na₂SO₄), evaporate the solvent in vacuo and purify by chromatography (hexane/ethyl acetate) to give the title compound as a white solid (595 mg, 82%).

Scheme B, step b: [4α, 7α(R*), 12bβ]-7-[(1-Oxo-2(S)-acetylthio-3-phenyl)-propylamino]-1,2,3,4,6,7,8,12b-octahydro-6-oxopyrido[2,1-a][2]benzazepine Dissolve thiolacetic acid (0.12 g, 1.7 mmol) in anhydrous-degassed methanol (10 mL) and treat with cesium carbonate (0.28 g, 0.86 mmol). Stir for 1 hour then evaporate the solvent in vacuo. Dissolve the resulting cesium salt in anhydrous-degassed dimethylformamide (6 mL) and treat with a solution of [4α, 7α(R*), 12bβ]-7-[(1-oxo-2(R)-bromo-3-phenylpropyl)amino]-1,2,3,4,6,7,8,12b-octahydro-6-oxopyrido[2,1-a][2]benzazepine (595 mg, 1.35 mmol) in anhydrous-degassed dimethylformamide (7 mL). Stir at room temperature for 2.5 hours, add water (50 mL) and extract with ethyl acetate (125 mL). Wash with brine (2×50 mL), dry (Na₂SO₄), evaporate the solvent in vacuo and purify by chromatography (hexane/ethyl acetate) to give the title compound as an off-white foam (538 mg, 91%).

EXAMPLE 4

[4α, 7α(R*), 12bβ]-7-[(1-Oxo-2(R)-acetylthio-3-phenylpropyl)amino]-1,2,3,4,6,7,8,12b-octahydro-6-oxopyrido[2,1-a][2]benzazepine Scheme B, step a: [4α, 7α(R*), 12bβ]-7-[(1-Oxo-2(S)-bromo-3-phenylpropyl)amino]-1,2,3,4,6,7,8,12b-octahydro-6-oxopyrido[2,1-a][2]benzazepine Slurry L-phenylalanine (23.6 g, 143 mmol), 49% hydrobromic acid (500 g), water (500 mL) and concentrated sulfuric acid (50 mL) and cool to −5° C. Add, by dropwise addition, a solution of sodium nitrite (9.87 g, 143 mmol) in water (70 mL) over a period of about 1 hour. Stir at −5° C. to 0° C. overnight extract into ethyl ether (3×250 mL), combine the organic phases and wash with water (1×) and brine (2×). Dry (MgSO₄) and evaporate the solvent in vacuo to give 3-phenyl-2(S)-bromopropionic acid as a yellow oil (26 g, 80%).

Dissolve [4α, 7α(R*), 12bβ]-7-(amino)-1,2,3,4,6,7,8,12b-octahydro-6-oxopyrido[2,1-a][2]benzazepine (0.38 mg, 1.65 mmol), 3-phenyl-2(S)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na₂SO₄), evaporate the solvent in vacuo and purify by chromatography (hexane/ethyl acetate) to give the title compound as a white solid (660 mg, 91%).

Scheme B, step b: [4α, 7α(R*), 12bβ]-7-[(1-Oxo-2(S)-acetylthio-3-phenyl)-propylamino]-1,2,3,4,6,7,8,12b-octahydro-6-oxopyrido[2,1-a][2]benzazepine Dissolve thiolacetic acid (0.1 mL, 1.9 mmol) in anhydrous-degassed methanol (10 mL) and treat with cesium carbonate (0.31 g, 0.95 mmol). Stir for 1 hour then evaporate the solvent in vacuo. Dissolve the resulting cesium salt in anhydrous-degassed dimethylformamide (6 mL) and treat with a solution of [4α, 7α(R*), 12bβ]-7-[(1-oxo-2(R)-bromo-3phenylpropyl)amino]-1,2,3,4,6,7,8,12b-octahydro-6-oxopyrido[2,1-a][2]benzazepine (660 mg, 1.50 mmol) in anhydrous-degassed dimethylformamide (7 mL). Stir at room temperature overnight, add water (50 mL) and extract with ethyl acetate (125 mL). Wash with brine (2×50 mL), dry (Na₂SO₄), evaporate the solvent in vacuo and purify by chromatography (hexane/ethyl acetate) to give the title compound as a pale rose foam (563 mg, 86%).

EXAMPLE 5

[4α, 7α(R*), 12bβ]-7-[(1-Oxo-2(R)-acetylthio-3-phenylpropyl)amino]-3,4,6,7,8,12b-hexahydro-6-oxo-1H-[1,4-]oxazino[3,4-a][2]benzazepine Scheme D, step a: (R*,R*)]-N-[2-(1,3-Dihydro-1,3-dioxo-2H-isoindol-2-yl)-1-oxo-3-phenylpropyl]-3,4-dihydro-2H-1,4-oxazine Wash sodium hydride (7.75 g, 191 mmol of a 59% dispersion in paraffin) 2 times with dry hexane (2×) under a nitrogen atmosphere. Add anhydrous dimethylformamide (90 mL) and cool with an ice/methanol bath. Add, by portionwise addition, ethanolamine hydrochloride (96.7 mmol), stir for 5 minutes and add potassium iodide (5.2 g, 32 mmol). Add, by dropwise addition, bromoacetaldehyde diethylacetal (14.5 mL, 96.7 mmol), remove the ice bath and stir for 8 hours at room temperature. Add to a solution of N-phthaloyl-(S)-phenylalanine (14.2 g, 48 mmol) and N-carbethoxy-2-ethoxy-1,2-dihydroquinoline (11.9 g, 48 mmol) in anhydrous tetrahydrofuran (40 mL). Stir for 18 hours at room temperature, partition between water (200 mL) and diethyl ether (200 mL) and separate the organic phase. Extract the aqueous phase with diethyl ether (200 mL), combine the organic phases and wash with 1N hydrochloric acid (2×200 mL), then saturated sodium hydrogen carbonate (2×200 mL), then brine (50 mL). Dry (MgSO4), filter and evaporate the solvent in vacuo to give the intermediate acetal.

Dissolve the intermediate acetal (30.3 mmol) in chloroform (500 mL) and add trifluoroacetic acid (4.5 mL). Reflux for 4 hours under a nitrogen atmosphere, cool and wash with saturated sodium hydrogen carbonate (300 mL) and filter through anhydrous MgSO4. Evaporate the solvent in vacuo and purify by chromatography to give the title compound.

Scheme D, step b: [4α, 7α(R*), 12bβ]-7-[(1,3-Dihydro-1,3-dioxo-2H-isoindol-2-yl)]-3,4,6,7,8,12b-hexahydro-6-oxo-1H[1,4]-oxazino[3,4-a][2]benzazepine Dissolve (R*,R*)]-N-[2-(1,3-Dihydro-1,3-dioxo-2H-isoindol-2-yl)-1-oxo-3-phenylpropyl]-3,4-dihydro-2H-1,4-oxazine (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na2SO4), evaporate the solvent in vacuo and purify by chromatography to give the title compound.

Scheme D, step c: [4α, 7α(R*), 12bβ]-7-(Amino)-3,4,6,7,8,12b-hexahydro-6-oxo-1H-[1,4]-oxazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4-]oxazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO4 and evaporate the solvent in vacuo to give the title compound.

Scheme B, step a: [4α, 7α(R*), 12bβ]-7-[(1-Oxo-2(S)-bromo-3-phenylpropyl)amino]-3,4,6,7,8,12b-hexahydro-6-oxo-1H-[1,4]-oxazino[3,4-a][2]benzazepine Dissolve [4α, 7α(R*), 12bβ]-7-(amino)-3,4,6,7,8,12b-hexahydro-6-oxo-1H-[1,4]-oxazino[3,4-a][2]benzazepine[4α, 7α(R*), 12bβ]-7-(amino)-1,2,3,3,6,7,8,12b-octahydro-6-oxopyrido[2,1-a][2]benzazepine (1.65 mmol), 3-phenyl-2(S)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na2SO4), evaporate the solvent in vacuo and purify by chromatography to give the title compound.

Scheme B, step b: [4α, 7α(R*), 12bβ]-7-[(1-Oxo-2(R)-acetylthio-3-phenyl)propylamino]-3,4,6,7,8,12b-hexahydro-6-oxo-1H-[1,4]-oxazino[3,4-a][2benzazepine Dissolve thiolacetic acid (0.12 g, 1.7 mmol) in anhydrous-degassed methanol (10 mL) and treat with cesium carbonate (0.28 g, 0.86 mmol). Stir for 1 hour then evaporate the solvent in vacuo. Dissolve the resulting cesium salt in anhydrous-degassed dimethylformamide (6 mL) and treat with a solution of [4α, 7α(R*), 12bβ]-7-[(1-oxo-2(S)-bromo-3-phenylpropyl)amino]-3,4,6,7,8,12b-hexahydro-6-oxo-1H-[1,4-]oxazino[3,4-a][2]benzazepine (1.35 mmol) in anhydrous-degassed dimethylformamide (7 mL). Stir at room temperature for 2.5 hours, add water (50 mL) and extract with ethyl acetate (125 mL). Wash with brine (2×50 mL), dry (Na2SO4), evaporate the solvent in vacuo and purify by chromatography to give the title compound.

EXAMPLE 6

[4α, 7α(R*), 12bβ]-7-[(1-Oxo-2(R)-thio-3-phenylpropyl)amino]-3,4,6,7,8,12b-hexahydro-6-oxo-1H-[1,4]-oxazino[3,4-a][2]benzazepine Dissolve [4α, 7α(R*), 12bβ]-7-[(1-oxo-2(R)-acetylthio-3-phenyl)propylamin]-3,4,6,7,8,12b-hexahydro-6-oxo-1H-[1,4-]oxazino[3,4-a][2]benzazepine (0.550 mmol) in a degassed mixture of tetrahydrofuran (5 mL) and methanol (5 mL). Cool in an ice bath and treat with lithium hydroxide (1 mL of a 1.0M solution). Stir under an argon atmosphere for 1 hour and add hydrochloric acid (1.5 mL of a 1M solution). Partition between methylene chloride (75 mL) and water (30 mL); separate the organic phase and dry (Na2SO4). Evaporate the solvent in vacuo and purify by chromatography to give the title compound.

EXAMPLE 7

4α, 7α(R*), 12bβ]-7-[(1-Oxo-2(R)-acetylthio-3-phenylpropyl)amino]-3,4,6,7,8,12b-hexahydro-6-oxo-1H-[1,4-]thiazino[3,4-a][2]benzazepine Scheme D, step a: (R*,R*)]-N-[2-(1,3-Dihydro-1,3-dioxo-2H-isoindol-2-yl)-1-oxo-3-phenylpropyl]-3,4-dihydro-2H-1,4-thiazine Wash sodium hydride (7.75 g, 191 mmol of a 59% dispersion in paraffin) 2 times with dry hexane (2×)

under a nitrogen atmosphere. Add anhydrous dimethylformamide (90 mL) and cool with an ice/methanol bath. Add, by portionwise addition, 2-aminoethanethiol hydrochloride (96.7 mmol), stir for 5 minutes and add potassium iodide (5.2 g, 32 mmol). Add, by dropwise addition, bromoacetaldehyde diethylacetal (14.5 mL, 96.7 mmol), remove the ice bath and stir for 8 hours at room temperature. Add to a solution of N-phthaloyl-(S)-phenylalanine (14.2 g, 48 mmol) and N-carbethoxy-2-ethoxy-1,2-dihydroquinoline (11.9 g, 48 mmol) in anhydrous tetrahydrofuran (40 mL). Stir for 18 hours at room temperature, partition between water (200 mL) and diethyl ether (200 mL) and separate the organic phase. Extract the aqueous phase with diethyl ether (200 mL), combine the organic phases and wash with 1N hydrochloric acid (2×200 mL), then saturated sodium hydrogen carbonate (2×200 mL), then brine (50 mL) Dry (MgSO₄), filter and evaporate the solvent in vacuo to give the intermediate acetal.

Dissolve the intermediate acetal (30.3 mmol) in chloroform (500 mL) and add trifluoroacetic acid (4.5 mL). Reflux for 4 hours under a nitrogen atmosphere, cool and wash with saturated sodium hydrogen carbonate (300 mL) and filter through anhydrous MgSO₄. Evaporate the solvent in vacuo and purify by chromatography to give the title compound.

Scheme D, step b: [4α, 7α(R*), 12bβ]-7-[(1,3-Dihydro-1,3-dioxo-2H-isoindol-2-yl)]-3,4,6,7,8,12b-hexahydro-6-oxo-1H-[1,4]-thiazino[3,4-a][2]benzazepine Dissolve (R*,R*)]-N-[2-(1,3-Dihydro-1,3-dioxo-2H-isoindol-2-yl)-1-oxo-3-phenylpropyl]-3,4-dihydro-2H-1,4-thiazine (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na₂SO₄), evaporate the solvent in vacuo and purify by chromatography to give the title compound.

Scheme D, step c: [4α, 7α(R*), 12bβ]-7-(Amino)-3,4,6,7,8,12b-hexahydro-6-oxo-1H-[1,4]-thiazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4-]thiazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO₄ and evaporate the solvent in vacuo to give the title compound.

Scheme B, step a: [4α, 7α(R*), 12bβ]-7-[(1-Oxo-2(S)-bromo-3-phenylpropyl)amino]-3,4,6,7,8,12b-hexahydro-6-oxo-1H-[1,4]-thiazino[3,4-a][2]benzazepine Dissolve [4α, 7α(R*), 12bβ]-7-(amino)-3,4,6,7,8,12b-hexahydro-6-oxo-1H-[1,4]-thiazino[3,4-a][2]benzazepine (1.65 mmol), 3-phenyl-2(S)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na₂SO₄), evaporate the solvent in vacuo and purify by chromatography to give the title compound.

Scheme B, step b: [4α, 7α(R*), 12bβ]-7-[(1-Oxo-2(R)-acetylthio-3-phenyl)-propylamino]-3,4,6,7,8,12b-hexahydro-6-oxo-1H-[1,4]-thiazino[3,4-a][2]benzazepine Dissolve thiolacetic acid (0.12 g, 1.7 mmol) in anhydrous-degassed methanol (10 mL) and treat with cesium carbonate (0.28 g, 0.86 mmol). Stir for 1 hour then evaporate the solvent in vacuo. Dissolve the resulting cesium salt in anhydrous-degassed dimethylformamide (6 mL) and treat with a solution of [4α, 7α(R*), 12bβ]-7-[(1-oxo-2(S)-bromo-3-phenylpropyl)amino]-3,4,6,7,8,12b-hexahydro-6-oxo-1H-[1,4]-thiazino[3,4-a][2]benzazepine (1.35 mmol) in anhydrous-degassed dimethylformamide (7 mL). Stir at room temperature for 2.5 hours, add water (50 mL) and extract with ethyl acetate (125 mL). Wash with brine (2×50 mL), dry (Na₂SO₄), evaporate the solvent in vacuo and purify by chromatography to give the title compound.

EXAMPLE 8

[4α, 7α(R*), 12bβ]-7-[(1-Oxo-2(R)-thio-3-phenylpropyl)amino]-3,4,6,7,8,12b-hexahydro-6-oxo-1H-[1,4]-thiazino[3,4-a][2]benzazepine Dissolve [4α, 7α(R*), 12bβ]-7-[(1-oxo-2(R)-acetylthio-3-phenylpropyl)amino]-3,4,6,7,8,12b-hexahydro-6-oxo-1H-[1,4]-thiazino[3,4-a][2]benzazepine (0.550 mmol) in a degassed mixture of tetrahydrofuran (5 mL) and methanol (5 mL). Cool in an ice bath and treat with lithium hydroxide (1 mL of a 1.0M solution). Stir under an argon atmosphere for 1 hour and add hydrochloric acid (1.5 mL of a 1M solution). Partition between methylene chloride (75 mL) and water (30 mL), separate the organic phase and dry (Na₂SO₄). Evaporate the solvent in vacuo and purify by chromatography to give the title compound.

EXAMPLE 9

[4α, 7α(R*), 12bβ]-7-[(1-Oxo-2(R)-acetylthio-3-azazino[3,4-a][2]benzazepine

Scheme D, step a: (R*,R*)]-N-[2-(1,3-Dihydro-1,3-dioxo-2H-isoindol-2-yl)-1-oxo-3-phenylpropyl]-3,4-dihydro-2H-4-trifluoracetyl-1,4-azazine Slurry N-phthaloyl-(S)-phenylalanine (2.0 g, 6.77 mmol) in methylene chloride (30 mL), cool to 0° C. and treat with N-hydroxysuccinimide (0.94 g, 8.1 mmol), then with 1-(3-dimethylaminopropyl)-3-ethylcarbodiimide hydrochloride (1.56 g, 8.1 mmol). Stir for 1 hour at 0° C. and at room temperature for 2.5 hours. Add methylene chloride (50 mL) and wash with 5% sulfuric acid (30 mL), then saturated sodium hydrogen carbonate (30 mL). Dry (Na₂SO₄) and evaporate the solvent in vacuo to give N-phthaloyl-(S)-phenylalanine, succinimide as a white solid (2.77 g).

Dissolve ethylenediamine (0.67 mL, 10 mmol) in methylene chloride (15 mL) and cool to −78° C. Add, by dropwise addition, a solution of N-phthaloyl-(S)-phenylalanine, succinimide (0.785 g, 2.0 mmol) in methylene chloride (5 mL). Stir at −78° C. for 1 hour, quench with water and allow to warm to room temperature. Partition between methylene chloride (100 mL) and water (30 mL), separate the organic phase and dry (Na₂SO₄). Evaporate the solvent in vacuo to give N-[2-(1,3-dihydro-1,3-dioxo-2H-isoindol-2-yl)-1-oxo-3-phenylpropyl]-ethylenediamine (80%).

Dissolve N-[2-(1,3-dihydro-1,3-dioxo-2H-isoindol-2-yl)-1-oxo-3-phenylpropyl]-ethylenediamine (2.0 mmol) in methylene chloride (25 mL) and cool in an ice bath. Treat with trifluoroacetic anhydride (0.42 mL, 3 mmol) followed by pyridine (0.24 L, 3.0 mmol) and stir at 0°-5° C. for 1 hour. Remove the ice bath and stir an additional 1.5 hours. Quench with ice water (25 mL), extract into methylene chloride (65 mL) and wash the organic phase with saturated sodium hydrogen carbonate. Dry (Na₂SO₄) and evaporate the solvent in vacuo. Purify by silica gel chromatography (3:2 ethylen acetate/hexane) to give 2-[N-[2-(1,3-dihydro-1,3-dioxo-2H-isoindol-2-yl)-1-oxo-3-phenylpropyl]]-1-[N-trifluoroacetyl]-ethylenediamine as a pale yellow solid (292 mg, 34%).

Mix 2-[N-[2-(1,3-dihydro-1,3-dioxo-2H-isoindol-2-yl)-1-oxo-3-phenylpropyl]]-1-[N-trifluoroacetyl]-ethylenediamine (290 mg, 0.669 mmol) in anhydrous dimethylformamide (5 mL) and treat with sodium hydride (21 mg, 0.7 mmol, 80% dispersion in oil). Stir for 10 minutes and add allyl bromide (0.1 mL, 1 mmol). Stir for 2 hours, add additional sodium hydride (21 mg) and stir for an additional 4 hours. Add saturated ammonium chloride solution (10 mL) and ethyl acetate (75 mL).

Separate the organic phase and wash with brine (25 mL). Dry (Na₂SO₄), evaporate the solvent in vacuo and purify by silic gel chromatography (3:2 hexane/ethyl acetate) to give the title compound (69 mg, 22%).

Scheme D, step b: [4α, 7α(R*), 12bβ]-7-[(1,3-Dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine Dissolve (R*,R*)]-N-[2-(1,3-Dihydro-1,3-dioxo-2H-isoindol-2-yl)-1-oxo-3-phenylpropyl]-3,4-dihydro-2H-4-trifluoracetyl-1,4-azazine (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na₂SO₄), evaporate the solvent in vacuo and purify by chromatography to give the title compound.

Scheme D, step c: [4α, 7α(R*), 12bβ]-7-(Amino)-3,4,6,7,8,12b-hexahydro-6-oxo-1H-4-t-butyloxycarbonyl-[1,4]-azazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine (9 mmol) in anhydrous tetrahydrofuran (30 mL) and treat with pyrrolidine (3.6 mmol). Stir at room temperature for 48 hours and evaporate the solvent in vacuo to give [4α, 7α(R*), 12bβ]-7-[o-pyrrolidinocarbonylbenzamide]-3,4,6,7,8,12b-hexahydro-6-oxo-1H-4-trifluoroacetyl-[1,4]-azazino[3,4-a][2]benzazepine.

Dissolve [4α, 7α(R*), 12bβ]-7-[o-pyrrolidinocarbonylbenzamide]-3,4,6,7,8,12b-hexahydro-6-oxo-1H-4-trifluoroacetyl-[1,4]-azazino[3,4-a][2]benzazepine (1.5 mmol) in a mixture of ethanol (3 mL) and acetone (3 mL). Add sodium borohydride (1.5 mmol) and stir at room temperature overnight. Pour into water (25 mL) and carefully neutralize with 1N hydrochloric acid. Extract into ethyl acetate (2×), dry (MgSO₄) and evaporate the solvent in vacuo to give [4α, 7α(R*), 12bβ]-7-[o-pyrrolidinocarbonylbenzamide]-3,4,6,7,8,12b-hexahydro-6-oxo-1H-[1,4]-azazino[3,4-a][2]benzazepine.

Dissolve [4α, 7α(R*), 12bβ]-7-[o-pyrrolidinocarbonylbenzamide]-3,4,6,7,8,12b-hexahydro-6-oxo-1H-[1,4]-azazino[3,4-a][2]benzazepine (1 mmol) in methanolic hydrochloric acid (5 mL) and stir at room temperature overnight. Evaporate the solvent in vacuo to give [4α, 7α(R*), 12bβ]-7-[(1,3-dihydro-1,3-dioxo-2H-isoindol-2-yl)]3,4,6,7,8,12b-hexahydro-6-oxo-1H-[1,4]-azazino[3,4-a][2]benzazepine.

Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4]-azazino[3,4-a][2]benzazepine (5 mmol) in 50/50 dioxane/water (25 mL) and buffer to pH 10 with 1N sodium hydroxide. Add, by dropwise addition, an ether solution of di-t-butyl dicarbonate (1.2 g, 5.5 mmol) at 10° C. Allow to warm to room temperature and buffer occasionally to retain pH 10. Acidify with a sodium citrate/citric acid buffer to pH 5, extract with ether (3×), dry (MgSO₄) and evaporate the solvent in vacuo to give [4α, 7α(R*), 12bβ]-7-[(1,3-dihydro-1,3-dioxo-2H-isoindol-2-yl)]-3,4,6,7,8,12b-hexahydro-6-oxo-1H-4-t-butyloxycarbonyl-[1,4]-azazino[3,4-a][2]benzazepine.

Dissolve [4α, 7α(R*), 12bβ]-7-[(1,3-dihydro-1,3-dioxo-2H-isoindol-2-yl)]-3,4,6,7,8,12b-hexahydro-6-oxo-1H-4-t-butyloxycarbonyl-[1,4]-azazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO₄ and evaporate the solvent in vacuo to give the title compound.

Scheme B, step a: [4α, 7α(R*), 12bβ]-7-[(1-Oxo-2(S)-bromo-3-phenylpropyl)amino]-3,4,6,7,8,12b-hexahydro-6-oxo-1H-4-t-butyloxycarbonyl-[1,4]-azazino[3,4-a][2]benzazepine Dissolve [4α, 7α(R*), 12bβ]-7-(amino)-3,4,6,7,8,12b-hexahydro-6-oxo-1H-4-t-butyloxycarbonyl-[1,4]-azazino[3,4-a][2]benzazepine (1.65 mmol), 3-phenyl-2(S)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na₂SO₄), evaporate the solvent in vacuo and purify by chromatography to give the title compound.

Scheme B, step b: [4α, 7α(R*), 12bβ]-7-[(1-Oxo-2(R)-acetylthio-3-phenyl)-propylamino]-3,4,6,7,8,12b-hexahydro-6-oxo-1H-4-t-butyloxycarbonyl-[1,4]-azazino[3,4-a][2]benzazepine Dissolve thiolacetic acid (0.12 g, 1.7 mmol) in anhydrous-degassed methanol (10 mL) and treat with cesium carbonate (0.28 g, 0.86 mmol). Stir for 1 hour then evaporate the solvent in vacuo. Dissolve the resulting cesium salt in anhydrous-degassed dimethylformamide (6 mL) and treat with a solution of [4α, 7α(R*), 12bβ]-7-[(1-oxo-2(S)-bromo-3-phenylpropyl)amino]-3,4,6,7,8,12b-hexahydro-6-oxo-1H-4-t-butyloxycarbonyl-[1,4]-azazino[3,4-a][2]benzazepine (1.35 mmol) in anhydrous-degassed dimethylformamide (7 mL). Stir at room temperature for 2.5 hours, add water (50 mL) and extract with ethyl acetate (125 mL). Wash with brine (2×50 mL), dry (Na₂SO₄), evaporate the solvent in vacuo and purify by chromatography to give the title compound.

Scheme B, optional step c: [4α, 7α(R*), 12bβ]-7-[(1-Oxo-2(R)-acetylthio-3-phenyl)-propylamino]-3,4,6,7,8,12b-hexahydro-6-oxo-1H-[1,4]-azazino[3,4-a][2]benzazepine Dissolve [4α, 7α(R*), 12bβ]-7-[(1-oxo-2(R)-acetylthio-3-phenyl)propylamino]-3,4,6,7,8,12b-hexahydro-6-oxo-1H-4-t-butyloxycarbonyl-[1,4]-azazino[3,4-a][2]benzazepine (10 mmol) in saturated methanolic hydrochloric acid (100 mL). Stir for several hours and evaporate the solvent in vacuo. Dissolve the residue in water and neutralize with saturated sodium hydrogen carbonate and extract with ethyl acetate. Dry (MgSO₄) and evaporate the solvent in vacuo. Purify by silica gel chromatography to give the title compound.

EXAMPLE 10

[4α, 7α(R*), 12bβ]-7-[(1-Oxo-2(R)-thio-3-phenylpropyl)amino]-3,4,6,7,8,12b-hexahydro-6-oxo-1H-[1,4]-azazino[3,4-a][2]benzazepine Dissolve [[4α, 7α(R*), 12bβ]-7-[(1-oxo-2(R)-acetylthio-3-phenylpropyl)amino]-3,4,6,7,8,12b-hexahydro-6-oxo-1H-[1,4]-azazino[3,4-a][2]benzazepine (0.550 mmol) in a degassed mixture of tetrahydrofuran (5 mL) and methanol (5 mL). Cool in an ice bath and treat with lithium hydroxide (1 mL of a 1.0M solution). Stir under an argon atmosphere for 1 hour and add hydrochloric acid (1.5 mL of a 1M solution). Partition between methylene chloride (75 mL) and water (30 mL), separate the organic phase and dry (Na₂SO₄). Evaporate the solvent in vacuo and purify by chromatography to give the title compound.

EXAMPLE 11

[6α(R*), 11bβ]-6-[(S)-(1-Oxo-2(R)-acetylthio-3-phenylpropyl)amino]-3,5,6,7,11b-heptahydro-5-oxo-pyrrolo[2,1-a][2]benzazepine Scheme D, step a: (R*,R*)-N-[2-(1,3-Dihydro-1,3-dioxo-2H-isoindol-2-yl)-1-oxo-3-phenylpropyl]-1,2,3-trihydro-2-pyrrole Mix 4-bromo-1-butene (0.209mol) and potassium cyanide (16.8 g, 0.257 mol) in ethylene glycol (85 mL) and heat at 100° C. for 2 hours. Cool, dilute with water (100 mL) and extract into ethyl ether (100 mL). Wash with saturated sodium hydrogen carbonate (35 mL), dry (Na₂SO₄) and distill to give 4-pentenylnitrile.

Suspend lithium aluminum hydride (6.5 g, 0.17 mol) in ethyl ether (350 mL) and add, by dropwise addition over 30 minutes, 4-pentenylnitrile (0.171 mol). Stir at room temperature for 2 hours, cool in an ice bath and add, by very slow addition, water (6.8 mL), then 20% sodium hydroxide (5.2 mL) then water (24 mL). Decant the ethereal phase and wash the white salts with ether. Combine the ethereal phases and distill to give 4-penteneamine.

Dissolve 4-pentenylamine (0.88 g, 8.9 mmol) in methylene chloride (50 mL) and treat first with N-phthaloyl-(S)-phenylalanine (2.95 g, 10.0 mmol), then with EEDQ (2.47 g, 10.0 mmol) and stir at room temperature for 6 hours. Evaporate the solvent in vacuo, dissolve the residue in ethyl acetate (75 mL) and wash with 5% sulfuric acid (25 mL), saturated sodium hydrogen carbonate (25 mL) and brine (25 mL). Dry (Na₂SO₄), evaporate the solvent in vacuo and purify by chromatography to give 2-(1,3-dihydro-1,3-dioxo-2H-isoindol-2-yl)-3-phenylpropionyl-4-pentenylamide.

Dissolve 2-(1,3-dihydro-1,3-dioxo-2H-isoindol-2-yl)-3-phenylpropionyl-4-pentenylamide (3.19 mmol) in methylene chloride (40 mL) and methanol (4 mL), cool to −78° C. and place under a nitrogen atmosphere. Treat with ozone until a blue color persists, degas with nitrogen for 20 minutes and add pyridine (0.2 mL). Quench with dimethylsulfide (4 mL) and stir overnight at room temperature. Dilute with methylene chloride (75 mL) and wash with 5% sulfuric acid (40 mL) and brine (40 mL). Dry (Na₂SO₄), evaporate the solvent in vacuo and purify by chromatography (hexane/ethyl acetate) to give 2-(1,3-dihydro-1,3-dioxo-2H-isoindol-2-yl)-3-phenylpropionyl-4-oxo-butylamide.

Dissolve 2-(1,3-dihydro-1,3-dioxo-2H-isoindol-2-yl)-3-phenylpropionyl-4-oxo-butylamide (0.404 mmol) in anhydrous methylene chloride (7 mL) and treat with trifluoroacetic acid (0.04 mL, 0.5 mmol). Stir at room temperature for 3 hours, partition between methylene chloride (25 mL) and saturated sodium hydrogen carbonate (15 mL). Dry (Na₂SO₄), evaporate the solvent in vacuo and purify by chromatography to give the title compound.

Scheme D, step b: [6α(R*), 11bβ]-6-[(S)-(1,3-Dihydro-1,3-dioxo-2H-isoindol-2-yl)]-3,5,6,7,11b-heptahydro-5-oxopyrrolo[2,1-a][2]benzazepine Dissolve (R*,R*)-N-[2-(1,3-dihydro-1,3-dioxo-2H-isoindol-2-yl)-1-oxo-3-phenylpropyl]-1,2,3-trihydro-2-pyrrole (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na₂SO₄), evaporate the solvent in vacuo and purify by chromatography to give the title compound.

Scheme D, step c: [6α(R*), 11bβ]-6-[(S)-Amino]-3,5,6,7,11b-heptahydro-5-oxo-pyrrolo[2,1-a][2]benzazepine Dissolve [6α(R*), 11bβ]-6-[(S)-(1,3-dihydro-1,3-dioxo-2H-isoindol-2-yl)]-3,5,6,7,11b-heptahydro-5-oxo-pyrrolo[2,1-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO₄ and evaporate the solvent in vacuo to give the title compound.

Scheme B, step a: [6α(R*), 11bβ]-6-[(S)-(1-Oxo-2(S)-bromo-3-phenylpropyl)amino]-3,5,6,7,11b-heptahydro-5-oxopyrrolo[2,1-a][2]benzazepine Dissolve [6α(R*), 11bβ]-6-[(S)-Amino]-3,5,6,7,11b-heptahydro-5-oxo-pyrrolo[2,1-a][2]benzazepine (1.65 mmol), 3-phenyl-2(S)-bromopropionic acid (567 mg, 2.48 mmol) and EEDQ (612 mg, 2.98 mmol) in methylene chloride (20 mL). Stir at room temperature for 18 hours, evaporate the solvent in vacuo and dissolve the residue in ethyl acetate (75 mL). Wash with 5% sulfuric acid (50 mL), saturated sodium hydrogen carbonate (50 mL) and brine (25 mL). Dry (Na$_2$SO$_4$), evaporate the solvent in vacuo and purify by chromatography to give the title compound.

Scheme B, step b: [6α(R*), 11bβ]-6-[(S)-(1-Oxo-2(R)-acetylthio-3-phenylpropyl)amino]-3,5,6,7,11b-heptahydro-5-oxo-pyrrolo[2,1-a][2]benzazepine Dissolve thiolacetic acid (0.12 g, 1.7 mmol) in anhydrous-degassed methanol (10 mL) and treat with cesium carbonate (0.28 g, 0.86 mmol). Stir for 1 hour then evaporate the solvent in vacuo. Dissolve the resulting cesium salt in anhydrous-degassed dimethylformamide (6 mL) and treat with a solution of [6α(R*), 11bβ]-6-[(S)-(1-oxo-2(S)-bromo-3-phenylpropyl)amino]-3,5,6,7,11b-heptahydro-5-oxopyrrolo[2,1-a][2]benzazepine (1.35 mmol) in anhydrous-degassed dimethylformamide (7 mL). Stir at room temperature for 2.5 hours, add water (50 mL) and extract with ethyl acetate (125 mL). Wash with brine (2×50 mL), dry (Na$_2$SO$_4$), evaporate the solvent in vacuo and purify by chromatography to give the title compound.

EXAMPLE 12

[6α(R*), 11bβ]-6-[(S)-(1-Oxo-2(R)-thio-3-phenylpropyl)amino]-3,5,6,7,11b-heptahydro-5-oxopyrrolo[2,1-a][2]benzazepine Dissolve [6α(R*), 11bβ]-6-[(S)-(1-oxo-2(R)-acetylthio-3-phenylpropyl)amino]-3,5,6,7,11b-heptahydro-5-oxopyrrolo[2,1-a][2]benzazepine (0.550 mmol) in a degassed mixture of tetrahydrofuran (5 mL) and methanol (5 mL). Cool in an ice bath and treat with lithium hydroxide (1 mL of a 1.0M solution). Stir under an argon atmosphere for 1 hour and add hydrochloric acid (1.5 mL of a 1M solution). Partition between methylene chloride (75 mL) and water (30 mL), separate the organic phase and dry (Na$_2$SO$_4$). Evaporate the solvent in vacuo and purify by chromatography to give the title compound.

The following compounds can be prepared by procedures analogous to those described above in Example 1–12:

[4α, 7α(R*), 12bβ]-7-[(1-Oxo-2(S)-benzoylthio-3-phenylpropyl)amino]-1,2,3,4,6,7,8,12b-octahydro-6-oxopyrido[2,1-a][2]benzazepine;

[4α, 7α(R*), 12bβ]-7-[(1-Oxo-2(S)-thio-3-phenylpropyl)amino]-1,2,3,4,6,7,8,12b-octahydro-6oxopyrido[2,1-a][2]benzazepine;

[4α, 7α(R*), 12bβ]-7-[(1-Oxo-2(S)-benzoylthio-3-phenylpropyl)amino]-3,4,6,7,8,12b-hexahydro-6-oxo-1H-[1,4]-oxazino[3,4-a][2]benzazepine;

[4α, 7α(R*), 12bβ]-7-[(1-Oxo-2(S)-thio-3-phenylpropyl)amino]-3,4,6,7,8,12b-hexahydro-6-oxo-1H-[1,4]-oxazino[3,4-a][2]benzazepine;

[4α, 7α(R*), 12bβ]-7-[(1-Oxo-2(S)-benzoylthio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(S)-thio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(S)-benzoylthio-3-phenylpropyl)amino]-3,4,6,7,8,12b-hexahydro-6-oxo-1H-[1,4]-azazino[3,4-a][2]benzazepine;

[4α, 7α(R*), 12bβ]-7-[(1-Oxo-2(S)-thio-3-phenylpropyl)amino]-3,4,6,7,8,12b-hexahydro-6-oxo-1H-[1,4]-azazino[3,4-a][2]benzazepine;

[6α(R*), 11bβ]-6-[(S)-(1-Oxo-2(S)-benzoylthio-3-phenylpropyl)amino]-3,5,6,7,11b-heptahydro-5-oxopyrrolo[2,1-a][2]benzazepine;

[6α(R*), 11bβ]-6-[(S)-(1-Oxo-2(S)-thio-3-phenylpropyl)amino]-3,5,6,7,11b-heptahydro-5-oxopyrrolo[2,1-a][2]benzazepine;

[4α, 7α(R*), 12bβ]-7-[(1-Oxo-2(S)-acetylthio-3-phenylpropyl)amino]-3,4,6,7,8,12b-hexahydro-6-oxo-1H-[1,4]-oxazino[3,4-a][2]benzazepine;

[4α, 7α(R*), 12bβ]-7-[(1-Oxo-2(S)-acetylthio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(S)-acetylthio-3-phenylpropyl)amino]-3,4,6,7,8,12b-hexahydro-6-oxo-1H-[1,4]-azazino[3,4-a][2]benzazepine;

[6α(R*), 11bβ]-6-[(S)-(1-Oxo-2(S)-acetylthio-3-phenylpropyl)amino]-3,5,6,7,11b-heptahydro-5-oxopyrrolo[2,1-a][2]benzazepine;

[4α, 7α(R*), 12bβ]-7-[(1-Oxo-2(R)-acetylthio-3-phenylpropyl)amino]-3,4,6,7,8,12b-hexahydro-6-oxo-1H-[1,4]-oxazino[3,4-a][2]benzazepine;

[4α, 7α(R*), 12bβ]-7-[(1-Oxo-2(R)-acetylthio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(R)-acetylthio-3-phenylpropyl)amino]-3,4,6,7,8,12b-hexahydro-6-oxo-1H-[1,4]-azazino[3,4-a][2]benzazepine;

[6α(R*), 11bβ]-6-[(S)-(1-Oxo-2(R)-acetylthio-3-phenylpropyl)amino]-3,5,6,7,11b-heptahydro-5-oxopyrrolo[2,1-a][2]benzazepine;

[4α, 7α(R*), 12bβ]-7-[(1-Oxo-2(S)-pivaloyloxymethylthio-3-phenylpropyl)amino]-1,2,3,4,6,7,8,12b-octahydro-6-oxopyrido[2,1-a][2]benzazepine;

[4α, 7α(R*), 12bβ]-7-[(1-Oxo-2(S)-pivaloyloxymethylthio-3-phenylpropyl)amino]-3,4,6,7,8,12b-hexahydro-6-oxo-1H-[1,4]-oxazino[3,4-a][2]benzazepine;

[4α, 7α(R*), 12bβ]-7-[(1-Oxo-2(S)-pivaloyloxymethylthio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(S)-pivaloyloxymethylthio-3-phenylpropyl)amino]-3,4,6,7,8,12b-hexahydro-6-oxo-1H-[1,4]-azazino[3,4-a][2]benzazepine;

[6α(R*), 11bβ]-6-[(S)-(1-Oxo-2(S)-pivaloyloxymethylthio-3-phenylpropyl)amino]-3,5,6,7,11b-heptahydro-5-oxopyrrolo[2,1-a][2]benzazepine;

[4α, 7α(R*), 12bβ]-7-[(1-Oxo-2(R)-pivaloyloxymethylthio-3-phenylpropyl)amino]-1,2,3,4,6,7,8,12b-octahydro-6oxopyrido[2,1-a][2]benzazepine;

[4α, 7α(R*), 12bβ]-7-[(1-Oxo-2(R)-pivaloyloxymethylthio-3-phenylpropyl)amino]-3,4,6,7,8,12b-hexahydro-6-oxo-1H-[1,4]-oxazino[3,4-a][2]benzazepine;

4α, 7α(R*), 12bβ]-7-[(1-Oxo-2(R)-pivaloyloxymethylthio-3-phenylpropyl)amino]-3,4,6,7,8,12b-hexahydro-6-oxo-1H-[1,4]-thiazino[3,4-a][2]benzazepine;

[4α, 7α(R*), 12bβ]-7-[(1-Oxo-2(R)-pivaloyloxymethylthio-3-phenylpropyl)amino]-3,4,6,7,8,12b-hexahydro-6-oxo-1H-[1,4]-azazino[3,4-a][2]benzazepine;

[6α(R*), 11bβ]-6-[(S)-(1-Oxo-2(R)-pivaloyloxymethylthio-3-phenylpropyl)amino]-3,5,6,7,11b-heptahydro-5-oxopyrrolo[2,1-a][2]benzazepine.

In a further embodiment, the present invention provides a method of inhibiting enkephalinase in a patient in need thereof comprising administering to said patient an effective enkephalinase inhibitory amount of a compound of Formula (I).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (1) wherein $B_1$ is hydrogen or alkoxy are preferred. The compounds of Formula (1) wherein $B_2$ is hydrogen or alkoxy are preferred. Compounds of Formula (1) wherein Z is —$CH_2$—, —O—, —S—, and a bond, $R_1$ is benzyl or methylenedioxybenzyl and $R_2$ is acetyl or pivaloyloxymethyl are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (1) are particularly preferred in the end-use application of the compounds of the present invention:

[4a, 7a(R*), 12bβ]-7-[(1-Oxo-2(R)-acetylthio-3-phenylpropyl)amino]-1,2,3,4,6,7,8,12b-octahydro-6oxopyrido[2,1-a][2]benzazepine and

[4a, 7a(R*), 12bβ]-7-[(1-Oxo-2(R)-thio-3-phenylpropyl)amino]-1,2,3,4,6,7,8,12b-octahydro-6oxopyrido[2,1-a][2]benzazepine.

What is claimed is:

1. A compound of the Formula

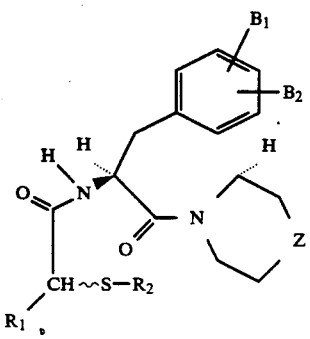

wherein
$B_1$ and $B_2$ are each independently hydrogen; hydroxy; —$OR_3$ wherein $R_3$ is a $C_1$-$C_4$ alkyl or an Ar-Y- group wherein Ar is phenyl or naphthyl group unsubstituted or substituted with from one to three substituents selected from the group consisting of methylenedioxy, hydroxy, $C_1$-$C_4$ alkoxy, amino, nitro, fluoro and chloro and Y is a $C_0$-$C_4$ alkyl; or, where $B_1$ and $B_2$ are attached to adjacent carbon atoms, $B_1$ and $B_2$ can be taken together with said adjacent carbons to form a benzene ring or methylenedioxy;

$R_1$ is hydrogen, $C_1$-$C_8$ alkyl, —$CH_2OCH_2CH_2OCH_3$ or an Ar-Y- group;

$R_2$ is hydrogen, acetyl, —$CH_2O$—$C(O)C(CH_3)_3$ or benzoyl; and

Z is —O—, —S—,

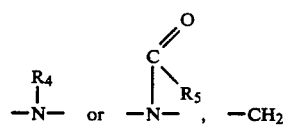

or a bond wherein $R_4$ is hydrogen, a $C_1$-$C_4$ alkyl or an Ar-Y- group and $R_5$ is —$CF_3$, $C_1$-$C_{10}$ alkyl or an Ar-Y- group; and the pharmaceutically acceptable salts and individual optical isomers thereof.

2. A compound according to claim 1 wherein Z is —$CH_2$—.

3. A compound according to claim 1 wherein Z is —O—.

4. A compound according to claim 1 wherein Z is —S—.

5. A compound according to claim 1 wherein Z is

6. A compound according to claim 1 wherein Z is

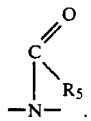

7. A compound according to claim 1 wherein Z is a bond.

8. A compound according to claim 2 wherein $R_2$ is hydrogen.

9. A compound according to claim 2 wherein $R_2$ is acetyl.

10. A compound according to claim 2 wherein $R_2$ is pivaloyloxymethyl.

11. A compound according to claim 8 wherein $R_1$ is an Ar-Y group.

12. A compound according to claim 9 wherein $R_1$ is an Ar-Y group.

13. A method of inhibiting enkephalinase in a patient in need thereof comprising administering to said patient an effective enkephalinase inhibitory amount of a compound of the formula

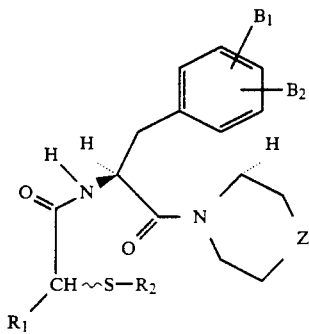

wherein $B_1$ and $B_2$ are each independently hydrogen; hydroxy; $-OR_3$ wherein $R_3$ is a $C_1-C_4$ alkyl or an Ar-Y- group wherein Ar is phenyl or naphthyl group unsubstituted or substituted with from one to three substituents selected from the group consisting of methylenedioxy, hydroxy, $C_1-C_4$ alkoxy, amino, nitro, fluoro and chloro and Y is a $C_0-C_4$ alkyl; or, where $B_1$ and $B_2$ are attached to adjacent carbon atoms, $B_1$ and $B_2$ can be taken together with said adjacent carbons to form a benzene ring or methylenedioxy;

$R_1$ is hydrogen, $C_1-C_8$ alkyl, $-CH_2OCH_2CH_2OCH_3$ or an Ar-Y- group;

$R_2$ is hydrogen, acetyl, $-CH_2O-C(O)C(CH_3)_3$ or benzoyl; and

Z is $-O-$, $-S-$,

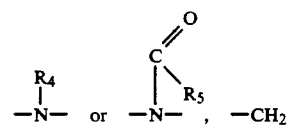

or a bond wherein $R_4$ is hydrogen, a $C_1-C_4$ alkyl or an Ar-Y- group and $R_5$ is $-CH_3$, $C_1-C_{10}$ alkyl or an Ar-Y- group; and the pharmaceutically acceptable salts and individual optical isomers thereof.

14. A method according to claim 13 wherein the patient is in need of an endorphin- or enkephalin-mediated analgesic effect.

15. A method according to claim 13 wherein the patient is in need of an ANP-mediated hypotensive effect.

16. A method according to claim 13 wherein the patient is in need of an ANP-mediated diuretic effect.

17. A method according to claim 13 wherein the patient is suffering from congestive heart failure.

18. A composition comprising an assayable amount of a compound of claim 1 in admixture or otherwise in association with an inert carrier.

19. A pharmaceutical composition comprising an effective immunosuppressive amount of a compound of claim 1 in admixture or otherwise in association with one or more pharmaceutically acceptable carriers or excipients.

20. A compound according to claim 1 wherein the compound is [4α, 7α(R*), 12bβ]-7-[(1-Oxo-2(R)-thio-3-phenylpropyl)amino]-1,2,3,4,6,7,8,12b-octahydro-6oxopyrido[2,1-a][2]benzazepine.

21. A compound according to claim 1 wherein the compound is [4α, 7α(R*), 12bβ]-7-[(1-Oxo-2(R)-acetylthio-3-phenylpropyl)amino]-1,2,3,4,6,7,8,12b-octahydro-6oxopyrido[2,1-a][2]benzazepine.

* * * * *

UNITED STATES PATENT AND TRADEMARK OFFICE
CERTIFICATE OF CORRECTION

PATENT NO. : 5,238,932
DATED : August 24, 1993
INVENTOR(S) : Gary A. Flynn, et al It is certified that error appears in the above-indentified patent and that said Letters Patent is hereby corrected as shown below:

```
Column 3, line 39 reads "ss", should read --"∽∽" --.
Column 14, line 48 reads "-2,3,", should read -- 1,2,3, --.
Column 16, line 60 reads "3phenylpropyl", should read -- 3-phenylpropyl
--.
Column 18, line 8reads "1,2,3,3,6,", should read -- 1,2,3,4,6, --.
Column 18 line 23 reads "[2benzazepine", should read -- [2]benzazepine
--.
Column 18, line 46 reads "propylamin]", should read -- propylamino] --.
Column 20 line 45 reads "-3-azazino[3,4-a][2]benzazepine", should read --
-3-phenylpropyl)amino]-3,4,6,7,8,12b-hexahydro-6-oxo-1H-[1,4]-
azazino[3,4-a][2]benzazepine --.
Column 25, line 51 reads "6oxopyrido", should read -- octahydro-6-
oxopyrido --.
Column 26, line 51 reads "6oxopyrido", should read -- -6-oxopyrido --.
Column 27, line 59 reads "circumstances In", should read --
circumstances. In --
Column 30, line 5 reads "6oxopyrido", should read -- -6-oxopyrido --.
Column 30, line 8  reads "6oxopyrido", should read -- -6-oxopyrido --.
Column 32, line 41  reads "6oxopyrido", should read -- -6-oxopyrido --.
Column 32, line 46  reads "6oxopyrido", should read -- -6-oxopyrido --.
```

Signed and Sealed this

Twenty-sixth Day of July, 1994

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,238,932

DATED : August 24, 1993

INVENTOR(S) : Gary A. Flynn & Alan M. Warshawsky

Page 1 of 12

It is certified that error appears in the above-indentified patent and that said Letters Patent is hereby corrected as shown below:

Column 2, line 13, column 30, line 18, and column 31, line 30 read:

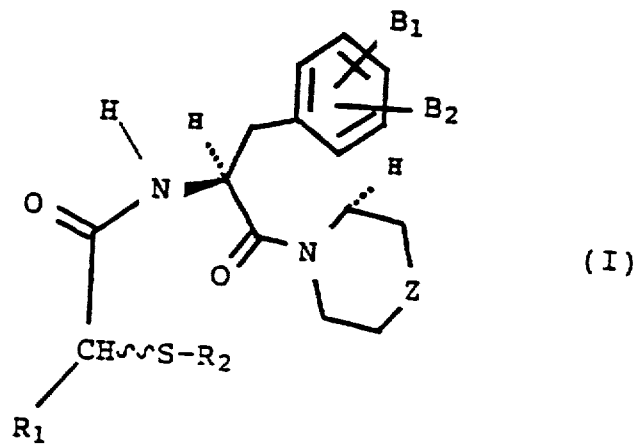

(I)

UNITED STATES PATENT AND TRADEMARK OFFICE
CERTIFICATE OF CORRECTION

PATENT NO. : 5,238,932
DATED : August 24, 1993
INVENTOR(S) : Gary A. Flynn & Alan M. Warshawsky It is certified that error appears in the above-indentified patent and that said Letters Patent is hereby corrected as shown below:

should read

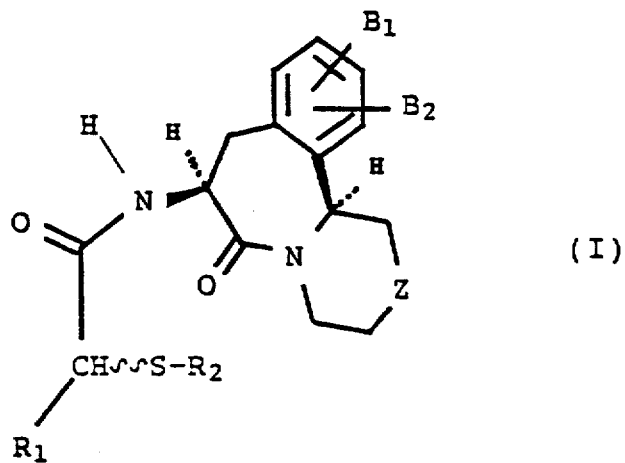

(I)

UNITED STATES PATENT AND TRADEMARK OFFICE
CERTIFICATE OF CORRECTION

PATENT NO. : 5,238,932
DATED : August 24, 1993
INVENTOR(S) : Gary A. Flynn & Alan M. Warshawsky It is certified that error appears in the above-indentified patent and that said Letters Patent is hereby corrected as shown below:

Column 4, lines 10, 22 and 35 (cf page 7, line 8-two places, and line 22) reads

Scheme A

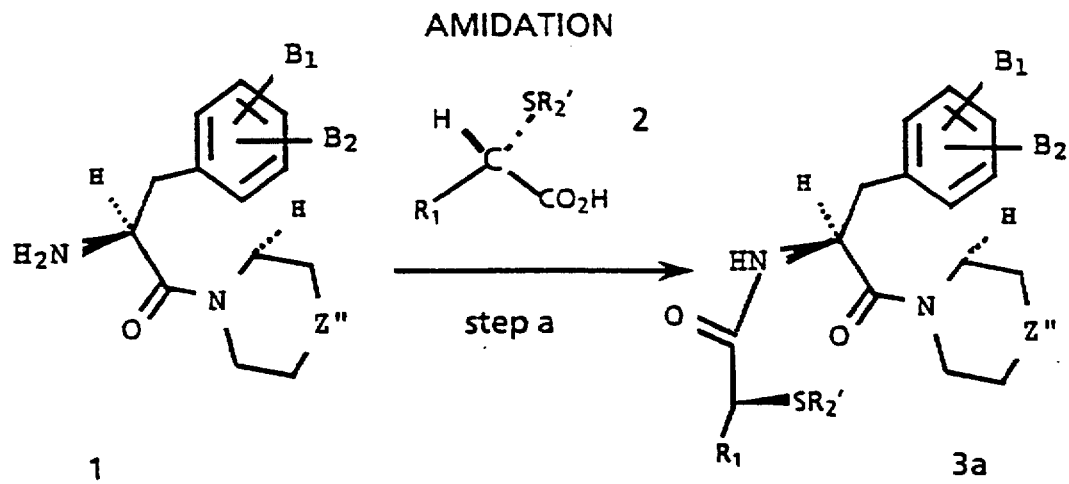

UNITED STATES PATENT AND TRADEMARK OFFICE
CERTIFICATE OF CORRECTION

PATENT NO. : 5,238,932  
DATED : August 24, 1993  
INVENTOR(S) : Gary A. Flynn & Alan M. Warshawsky It is certified that error appears in the above-indentified patent and that said Letters Patent is hereby corrected as shown below:

shoud read  optional step b

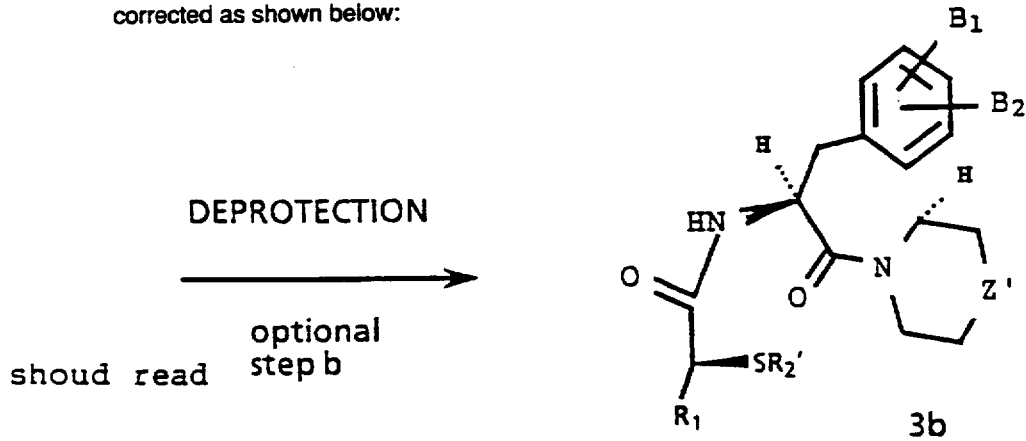

Scheme A

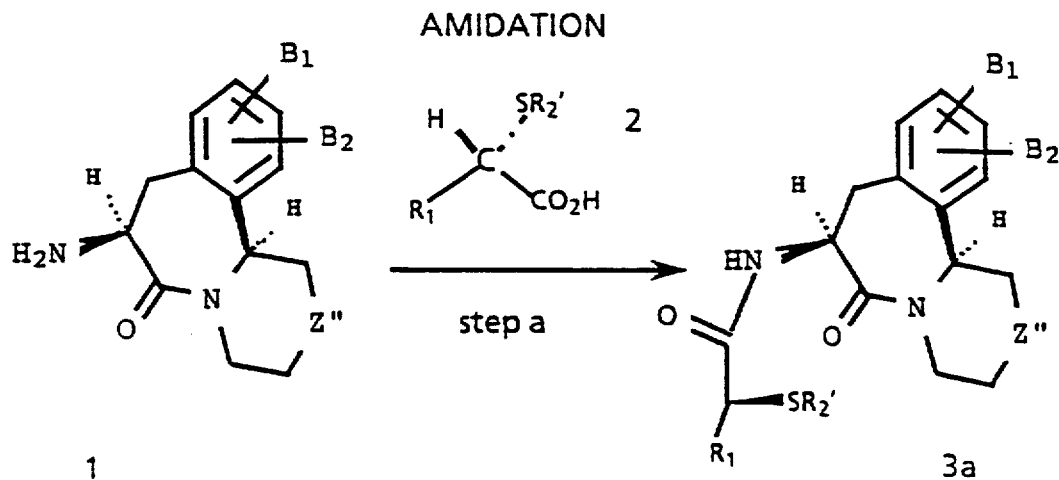

UNITED STATES PATENT AND TRADEMARK OFFICE
CERTIFICATE OF CORRECTION

PATENT NO. : 5,238,932  
DATED : August 24, 1993  
INVENTOR(S) : Gary A. Flynn & Alan M. Warshawsky Page 5 of 12

It is certified that error appears in the above-indentified patent and that said Letters Patent is hereby corrected as shown below:

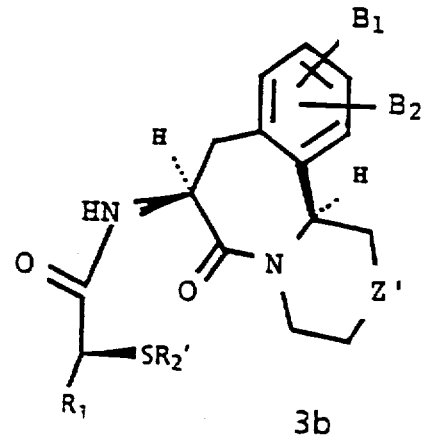

DEPROTECTION
⎯⎯⎯⎯⎯⎯⎯⎯→
optional step b

UNITED STATES PATENT AND TRADEMARK OFFICE
CERTIFICATE OF CORRECTION

PATENT NO. : 5,238,932

DATED : August 24, 1993

INVENTOR(S) : Gary A. Flynn & Alan M. Warshawsky

Page 6 of 12

It is certified that error appears in the above-indentified patent and that said Letters Patent is hereby corrected as shown below:

Column 7, lines 35, 47, and 60 (cf page 14, line 8-2 places, and line 20) reads

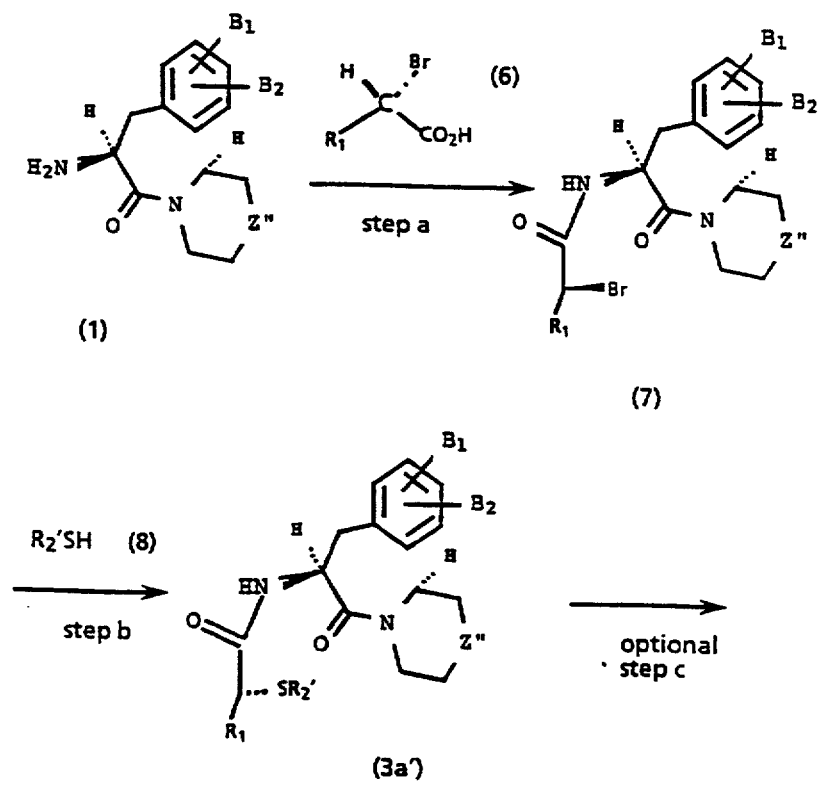

Scheme B

UNITED STATES PATENT AND TRADEMARK OFFICE
CERTIFICATE OF CORRECTION

PATENT NO. : 5,238,932
DATED : August 24, 1993
INVENTOR(S) : Gary A. Flynn & Alan M. Warshawsky It is certified that error appears in the above-indentified patent and that said Letters Patent is hereby corrected as shown below:

should read

Scheme B

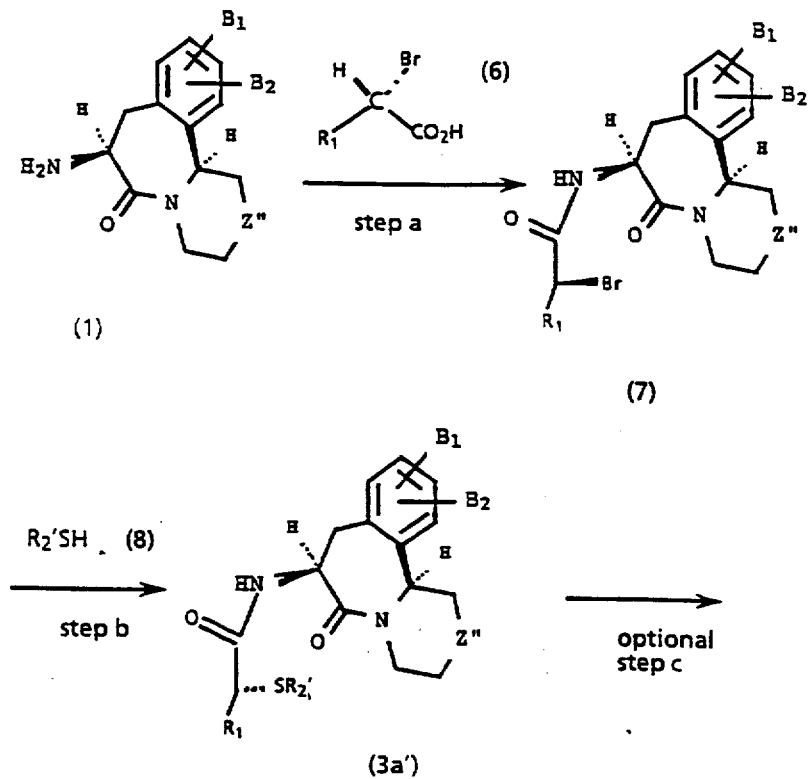

UNITED STATES PATENT AND TRADEMARK OFFICE
CERTIFICATE OF CORRECTION

PATENT NO. : 5,238,932

DATED : August 24, 1993

INVENTOR(S) : Gary A. Flynn & Alan M. Warshawsky

Page 8 of 12

It is certified that error appears in the above-indentified patent and that said Letters Patent is hereby corrected as shown below:

Column 8, line 7 (cf page 15, line 8) reads

Scheme B Cont.

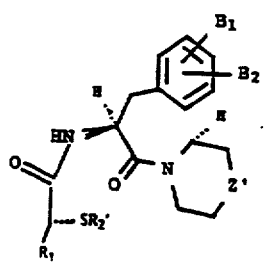

(3b')

should read

Scheme B Cont.

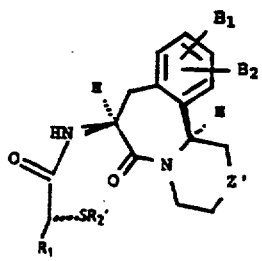

(3b')

UNITED STATES PATENT AND TRADEMARK OFFICE
CERTIFICATE OF CORRECTION

PATENT NO. : 5,238,932
DATED : August 24, 1993
INVENTOR(S) : Gary A. Flynn & Alan M. Warshawsky It is certified that error appears in the above-indentified patent and that said Letters Patent is hereby corrected as shown below:

Column 9 & 10 line 23 (2 places) and line 42 (cf page 19, line 6-2 places, and line 22) reads Scheme C

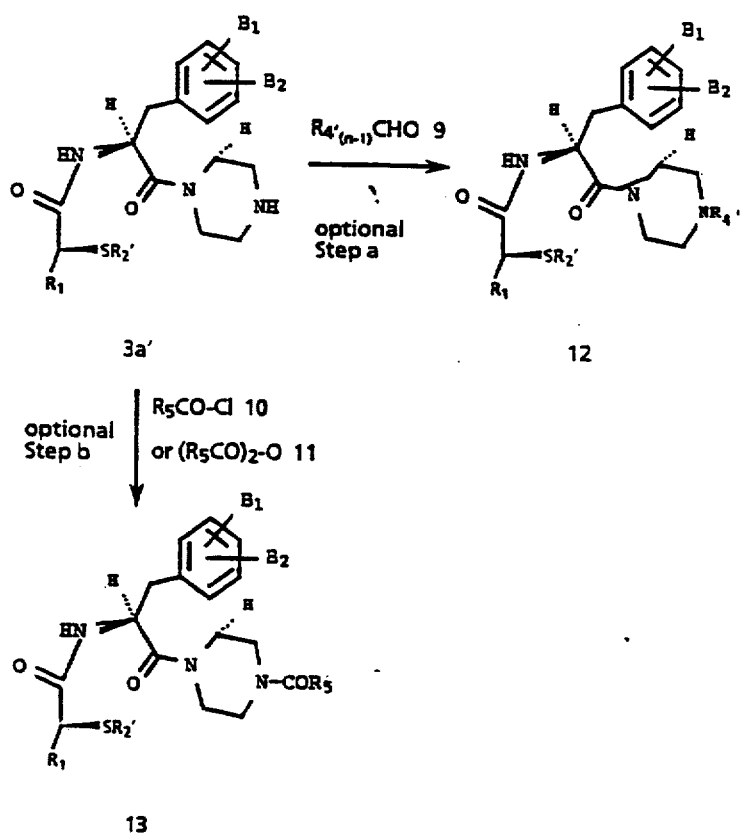

UNITED STATES PATENT AND TRADEMARK OFFICE
CERTIFICATE OF CORRECTION

PATENT NO. : 5,238,932

DATED : August 24, 1993

INVENTOR(S) : Gary A. Flynn & Alan M. Warshawsky

It is certified that error appears in the above-indentified patent and that said Letters Patent is hereby corrected as shown below:

should read

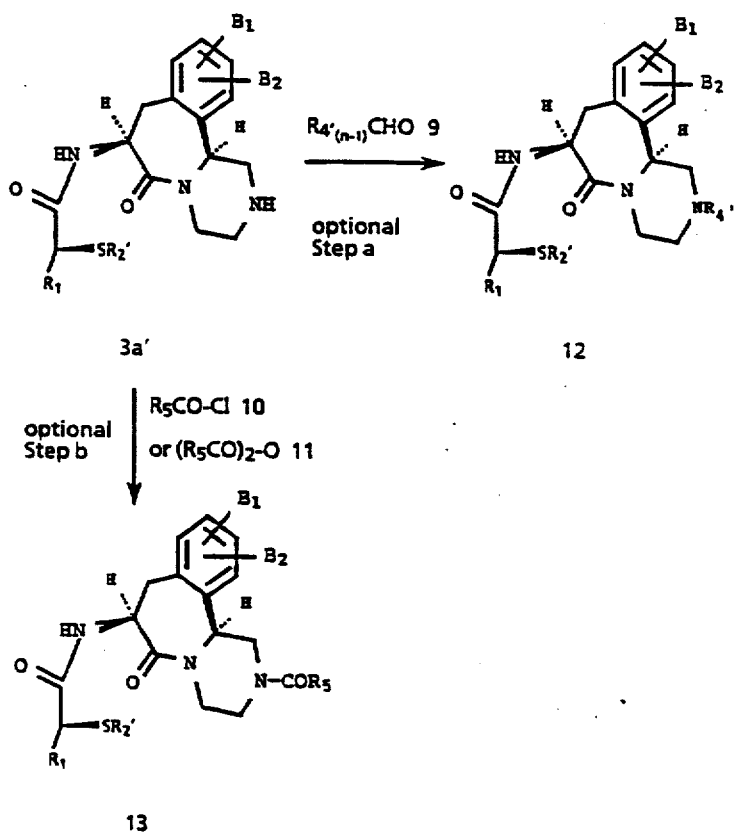

Scheme C

//! UNITED STATES PATENT AND TRADEMARK OFFICE
CERTIFICATE OF CORRECTION

PATENT NO. : 5,238,932
DATED : August 24, 1993
INVENTOR(S) : Gary A. Flynn & Alan M. Warshawsky It is certified that error appears in the above-indentified patent and that said Letters Patent is hereby corrected as shown below:

Column 12, line 22 and 35 (cf page 22, lines 18 and 26) reads

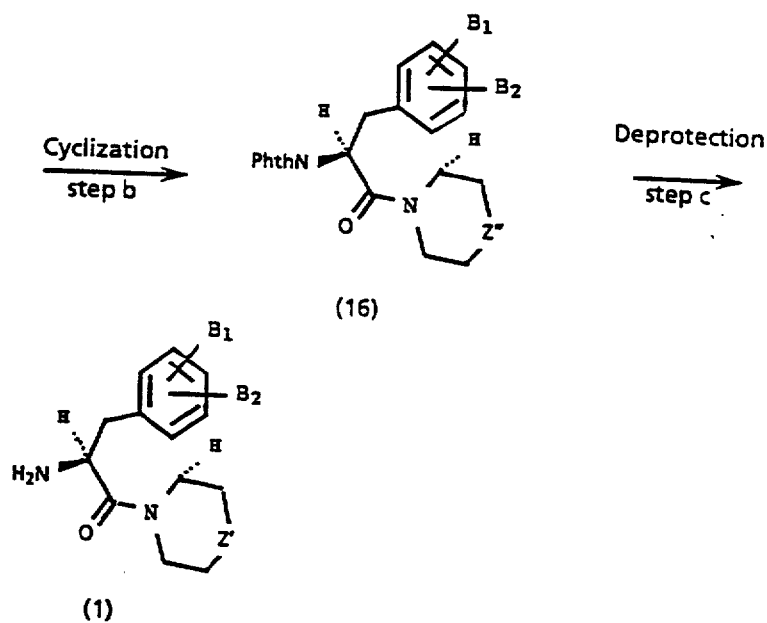

UNITED STATES PATENT AND TRADEMARK OFFICE
CERTIFICATE OF CORRECTION

PATENT NO. : 5,238,932  Page 12 of 12
DATED : August 24, 1993
INVENTOR(S) : Gary A. Flynn & Alan M. Warshawsky It is certified that error appears in the above-indentified patent and that said Letters Patent is hereby corrected as shown below:

should read

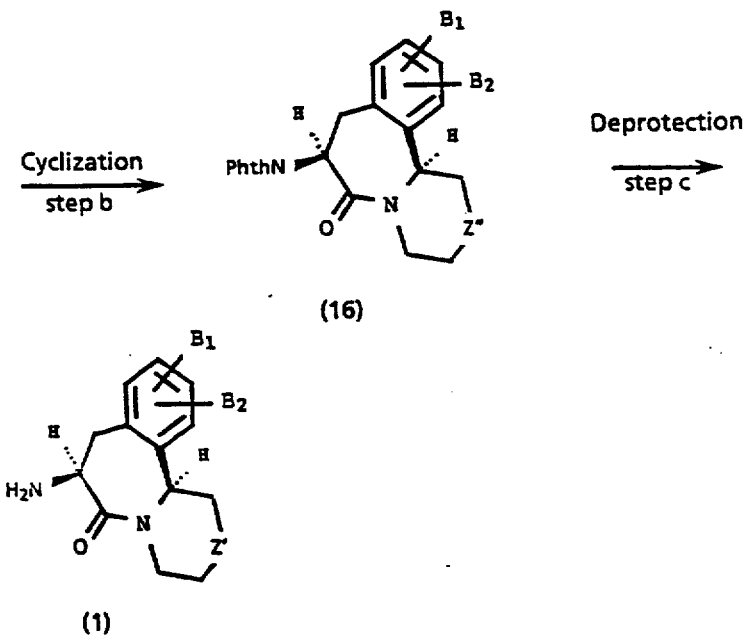

Signed and Sealed this

Twenty-eight Day of February, 1995

Attest:

BRUCE LEHMAN

Attesting Officer   Commissioner of Patents and Trademarks